United States Patent
Jin et al.

(10) Patent No.: US 10,402,074 B2
(45) Date of Patent: Sep. 3, 2019

(54) ULTRASOUND IMAGING APPARATUS AND METHOD OF CONTROLLING THE SAME

(71) Applicant: SAMSUNG MEDISON CO., LTD., Gangwon-do (KR)

(72) Inventors: Gil-Ju Jin, Seoul (KR); Mi Jeoung Ahn, Seoul (KR); Yuri Kim, Seoul (KR); Jae Moon Jo, Seongnam-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 663 days.

(21) Appl. No.: 14/945,212

(22) Filed: Nov. 18, 2015

(65) Prior Publication Data
US 2016/0139789 A1    May 19, 2016

Related U.S. Application Data

(60) Provisional application No. 62/081,475, filed on Nov. 18, 2014.

(30) Foreign Application Priority Data

May 6, 2015    (KR) .......................... 10-2015-0062990

(51) Int. Cl.
G06F 3/0488    (2013.01)
G06F 3/0484    (2013.01)
(Continued)

(52) U.S. Cl.
CPC .......... G06F 3/04847 (2013.01); A61B 8/463 (2013.01); A61B 8/464 (2013.01);
(Continued)

(58) Field of Classification Search
CPC . G06F 3/04847; G06F 3/04842; G06F 3/0488
See application file for complete search history.

(56) References Cited

U.S. PATENT DOCUMENTS

| 5,482,045 A | 1/1996 | Rust et al. |
| 8,016,759 B2 * | 9/2011 | Lee .......................... A61B 8/00 600/443 |

(Continued)

FOREIGN PATENT DOCUMENTS

| EP | 2 710 960 A1 | 3/2014 |
| EP | 2742868 A1 | 6/2014 |

OTHER PUBLICATIONS

European Office Action dated Jul. 20, 2017 issued in European Patent Application No. 15178878.3.
(Continued)

*Primary Examiner* — William L Bashore
*Assistant Examiner* — Nathan K Shrewsbury
(74) *Attorney, Agent, or Firm* — Morgan, Lewis & Bockius LLP

(57) ABSTRACT

Provided are an ultrasound imaging apparatus and a method of controlling the same, and more specifically, to a technique for displaying a gain compensation regulating unit including a time gain compensation (TGC) regulating unit or a lateral gain compensation (LGC) regulating unit corresponding to the set ROI when a region of interest (ROI) in an ultrasound image is set. The ultrasound imaging apparatus according to the embodiment includes an input unit configured to receive a command of setting a region of interest (ROI) in an ultrasound image; and a display unit including a first region on which the ultrasound image is displayed and a second region on which a gain compensation regulating unit configured to change a gain compensation value of the ultrasound image is displayed, wherein, when the command of setting the ROI in the ultrasound image displayed on the first region is input, the display unit displays only a gain compensation regulating unit corresponding to the input ROI in the ultrasound image on the second region.

25 Claims, 20 Drawing Sheets

(51) Int. Cl.
    *G06T 3/40*         (2006.01)
    *G06T 3/60*         (2006.01)
    *G06T 7/00*         (2017.01)
    *G06T 5/00*         (2006.01)
    *A61B 8/00*        (2006.01)
    *G01S 7/52*         (2006.01)
    *G06T 7/50*         (2017.01)
    *G06T 7/90*         (2017.01)

(52) U.S. Cl.
    CPC .............. *A61B 8/465* (2013.01); *A61B 8/467* (2013.01); *A61B 8/469* (2013.01); *G01S 7/52033* (2013.01); *G01S 7/52073* (2013.01); *G01S 7/52074* (2013.01); *G06F 3/04883* (2013.01); *G06T 3/40* (2013.01); *G06T 3/60* (2013.01); *G06T 5/009* (2013.01); *G06T 7/0012* (2013.01); *G06T 7/50* (2017.01); *G06T 7/90* (2017.01); *A61B 8/4405* (2013.01); *A61B 8/466* (2013.01); *G06T 2200/24* (2013.01); *G06T 2207/10132* (2013.01); *G06T 2207/20104* (2013.01); *G06T 2207/20208* (2013.01)

(56) References Cited

U.S. PATENT DOCUMENTS

| | | | | |
|---|---|---|---|---|
| 9,398,190 | B2* | 7/2016 | Ryan | H04N 1/387 |
| 2004/0015079 | A1* | 1/2004 | Berger | A61B 8/546 |
| | | | | 600/437 |
| 2005/0012825 | A1* | 1/2005 | Kimber | G06T 5/008 |
| | | | | 348/216.1 |
| 2005/0059892 | A1* | 3/2005 | Dubois | A61B 8/08 |
| | | | | 600/443 |
| 2005/0222871 | A1* | 10/2005 | Motoki | G06F 19/321 |
| | | | | 705/2 |
| 2006/0078225 | A1* | 4/2006 | Pearson | G01J 3/02 |
| | | | | 382/286 |
| 2007/0092492 | A1* | 4/2007 | Matsuda | A61L 27/3804 |
| | | | | 424/93.7 |
| 2007/0230759 | A1* | 10/2007 | Tamura | G01S 7/52033 |
| | | | | 382/128 |
| 2007/0232907 | A1* | 10/2007 | Pelissier | A61B 8/00 |
| | | | | 600/437 |
| 2008/0088719 | A1* | 4/2008 | Jacob | H04N 5/2256 |
| | | | | 348/241 |
| 2008/0139932 | A1 | 6/2008 | Lee et al. | |
| 2009/0309960 | A1* | 12/2009 | Park | G01J 3/02 |
| | | | | 348/61 |
| 2011/0043434 | A1* | 2/2011 | Roncalez | G06F 3/04847 |
| | | | | 345/3.1 |
| 2011/0276283 | A1 | 11/2011 | Lee et al. | |
| 2012/0027282 | A1* | 2/2012 | Yoshikawa | A61B 8/06 |
| | | | | 382/131 |
| 2013/0208132 | A1* | 8/2013 | Ryan | G01C 21/206 |
| | | | | 348/207.11 |
| 2013/0249842 | A1 | 9/2013 | Vama | |
| 2014/0088428 | A1* | 3/2014 | Yang | A61B 8/4444 |
| | | | | 600/443 |
| 2015/0057541 | A1 | 2/2015 | Yang et al. | |
| 2015/0342572 | A1* | 12/2015 | Tahmasebi Maraghoosh | A61B 8/0841 |
| | | | | 600/424 |
| 2015/0376478 | A1* | 12/2015 | Okamoto | C09J 4/00 |
| | | | | 156/64 |
| 2016/0106394 | A1* | 4/2016 | Kang | G06F 3/041 |
| | | | | 600/437 |

OTHER PUBLICATIONS

Extended European Search Report issued in European Application No. 15178878.3 dated Apr. 22, 2016.
European Communication dated Apr. 3, 2018 issued in European Patent Application No. 15 178 878.3.

\* cited by examiner (a)

(b)

(a)

(b)

(a)

(b)

(a)

(b)

(a)

(b)

(a)

(b)

(a)

(b)

(a)

(b)

ULTRASOUND IMAGING APPARATUS AND METHOD OF CONTROLLING THE SAME

CROSS-REFERENCE TO RELATED APPLICATION

This application claims priority to and the benefit of Korean Patent Application No. 10-2015-0062990, filed on May 6, 2015 in the Korean Intellectual Property Office and U.S. 62/081,475, filed on Nov. 18, 2014 in the United States Patent and Trademark Office, the disclosure of which is incorporated herein by reference.

BACKGROUND

1. Field

Embodiments of the present invention relate to an ultrasound imaging apparatus and a method of controlling the same, and more specifically, to a technique for displaying a gain compensation regulating unit including a time gain compensation (TGC) regulating unit or a lateral gain compensation (LGC) regulating unit corresponding to the set ROI when a region of interest (ROI) in an ultrasound image is set.

2. Description of the Related Art

An ultrasound imaging apparatus is an apparatus that radiates an ultrasound signal generated from a transducer of a probe to a target area inside a body from a body surface of a subject, receives information on a reflected ultrasound signal (ultrasound echo signal), obtains a tomogram of soft tissues of an area inside the subject or an image of blood flow in a non-invasive manner, and uses the obtained result for medical purposes such as observation of an inside of the subject, detection of a foreign material, and measurement of injuries.

The ultrasound imaging apparatus is advantageous in that it is small and inexpensive, can display in real time, and is highly safe because it involves no exposure to radiation, compared to other imaging diagnostic apparatuses such as an X-ray diagnostic apparatus, an X-ray computerized tomography (CT) scanner, a magnetic resonance imaging (MRI) apparatus, and a nuclear diagnostic apparatus. Due to these advantages, ultrasound imaging apparatuses are being widely used together with other imaging diagnostic apparatuses.

Meanwhile, in order to observe the subject, obtaining of an optimal ultrasound image vividly showing the subject is necessary. For this purpose, a user may regulate values of image parameters (a gain, a dynamic range (DR), time gain compensation (TGC), and lateral gain compensation (LGC)) to adjust brightness, a resolution, contrast and the like of an ultrasound image.

SUMMARY

A TGC or LGC regulating unit corresponding to a region of interest (ROI), set by a user, in an ultrasound image is displayed in order to regulate TGC or LGC of the ultrasound image, and thus TGC or LGC of a corresponding region can be regulated accurately and precisely.

According to an aspect of the present invention, there is provided an ultrasound imaging apparatus, including an input unit configured to receive a command of setting a region of interest (ROI) in an ultrasound image; and a display unit including a first region on which the ultrasound image is displayed and a second region on which a gain compensation regulating unit configured to change a gain compensation value of the ultrasound image is displayed, wherein, when the command of setting the ROI in the ultrasound image displayed on the first region is input, the display unit displays only a gain compensation regulating unit corresponding to the input ROI in the ultrasound image on the second region.

The ROI in the ultrasound image may be a region set by enlarging, reducing, expanding or rotating the ultrasound image, and when the ROI is set, a screen displayed on the display unit may be changed.

The gain compensation regulating unit may include at least one of a time gain compensation (TGC) regulating unit and a lateral gain compensation (LGC) regulating unit.

The display unit may display an increased or decreased level of the gain compensation regulating unit corresponding to the ROI in the ultrasound image such that gain compensation of the ROI in the ultrasound image is finely regulated.

The display unit may emphasize and display a display mode of the gain compensation regulating unit corresponding to the ROI in the ultrasound image, and emphasizing and displaying the gain compensation regulating unit may include displaying the gain compensation regulating unit corresponding to the ROI in the ultrasound image by changing a color thereof.

The display unit may display the ROI in the ultrasound image on the first region and display the ROI in the ultrasound image and the gain compensation regulating unit corresponding to the ROI in the ultrasound image in an overlapping manner.

The command of setting the ROI in the ultrasound image may include a command of enlarging or reducing a specific area in the ultrasound image.

The ultrasound imaging apparatus may further include a sub display panel configured to display an ultrasound image set as the ROI and the gain compensation regulating unit corresponding to the ROI in the ultrasound image, wherein the display unit may display an entire ultrasound image before the ROI in the ultrasound image is set and a gain compensation regulating unit corresponding thereto, and wherein the sub display panel may display the ROI in the ultrasound image and the gain compensation regulating unit corresponding to the ROI in the ultrasound image.

The sub display panel may display the ROI in the ultrasound image and the gain compensation regulating unit corresponding to the ROI in the ultrasound image in an overlapping manner.

The display unit and the sub display panel may include a touch panel in which a user inputs a touch command of setting the ROI in the ultrasound image and touches the gain compensation regulating unit corresponding to the ROI in the displayed ultrasound image and thus the gain compensation value corresponding to the ultrasound image set as the ROI may be regulated.

The display unit may display at least one of a TGC regulating unit configured to regulate a TGC value corresponding to a depth direction of the ultrasound image set as the ROI and an LGC regulating unit configured to regulate an LGC value corresponding to a lateral direction.

The display unit may display at least one of a TGC regulating object and a TGC regulating line configured to regulate a TGC value corresponding to a depth direction of the ultrasound image set as the ROI.

The display unit may display at least one of an LGC regulating object and an LGC regulating line configured to regulate an LGC value corresponding to a lateral direction of the ultrasound image set as the ROI.

The ultrasound imaging apparatus may further include a processor configured to perform control such that, when the command of setting the ROI in the ultrasound image displayed on the first region of the display unit is input, the gain compensation regulating unit corresponding to the input ROI in the ultrasound image is displayed on the second region.

The ultrasound imaging apparatus may further include a memory configured to store information on the input ROI in the ultrasound image and the gain compensation regulating unit corresponding to the input ROI in the ultrasound image.

According to another aspect of the present invention, there is provided a method of controlling an ultrasound imaging apparatus including a display unit having a first region on which an ultrasound image is displayed and a second region on which a gain compensation regulating unit configured to change a gain compensation value of the ultrasound image is displayed, the method including: receiving a command of setting a region of interest (ROI) in the ultrasound image displayed on the first region; and displaying only a gain compensation regulating unit corresponding to the input ROI in the ultrasound image on the second region.

The displaying of the gain compensation regulating unit corresponding to the input ROI in the ultrasound image may include displaying an increased or decreased level of the gain compensation regulating unit corresponding to the ROI in the ultrasound image such that gain compensation of the ROI in the ultrasound image is finely regulated.

The displaying of the gain compensation regulating unit corresponding to the input ROI in the ultrasound image may include emphasizing and displaying a display mode of the gain compensation regulating unit corresponding to the ROI in the ultrasound image, and the emphasizing and displaying of the gain compensation regulating unit may include displaying the gain compensation regulating unit corresponding to the ROI in the ultrasound image by changing a color thereof.

The displaying of the gain compensation regulating unit corresponding to the input ROI in the ultrasound image may include displaying the ROI in the ultrasound image displayed on the first region and the gain compensation regulating unit corresponding to the ROI in the ultrasound image in an overlapping manner.

The receiving of the command of setting the ROI in the ultrasound image may include a command of enlarging or reducing a specific area in the ultrasound image.

The gain compensation regulating unit may include at least one of a time gain compensation (TGC) regulating unit and a lateral gain compensation (LGC) regulating unit, and the displaying of the gain compensation regulating unit corresponding to the input ROI in the ultrasound image may include displaying at least one of a TGC regulating unit configured to regulate a TGC value corresponding to a depth direction of the ultrasound image set as the ROI and an LGC regulating unit configured to regulate an LGC value corresponding a lateral direction.

The displaying of the TGC regulating unit corresponding to the input ROI in the ultrasound image may include displaying at least one of a TGC regulating object and a TGC regulating line configured to regulate a TGC value corresponding to a depth direction of the ultrasound image set as the ROI.

The displaying of the LGC regulating unit corresponding to the input ROI in the ultrasound image may include displaying at least one of an LGC regulating object and an LGC regulating line configured to regulate an LGC value corresponding to a lateral direction in the ultrasound image set as the ROI.

The method may further include storing information on the input ROI in the ultrasound image and the gain compensation regulating unit corresponding to the input ROI in the ultrasound image.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
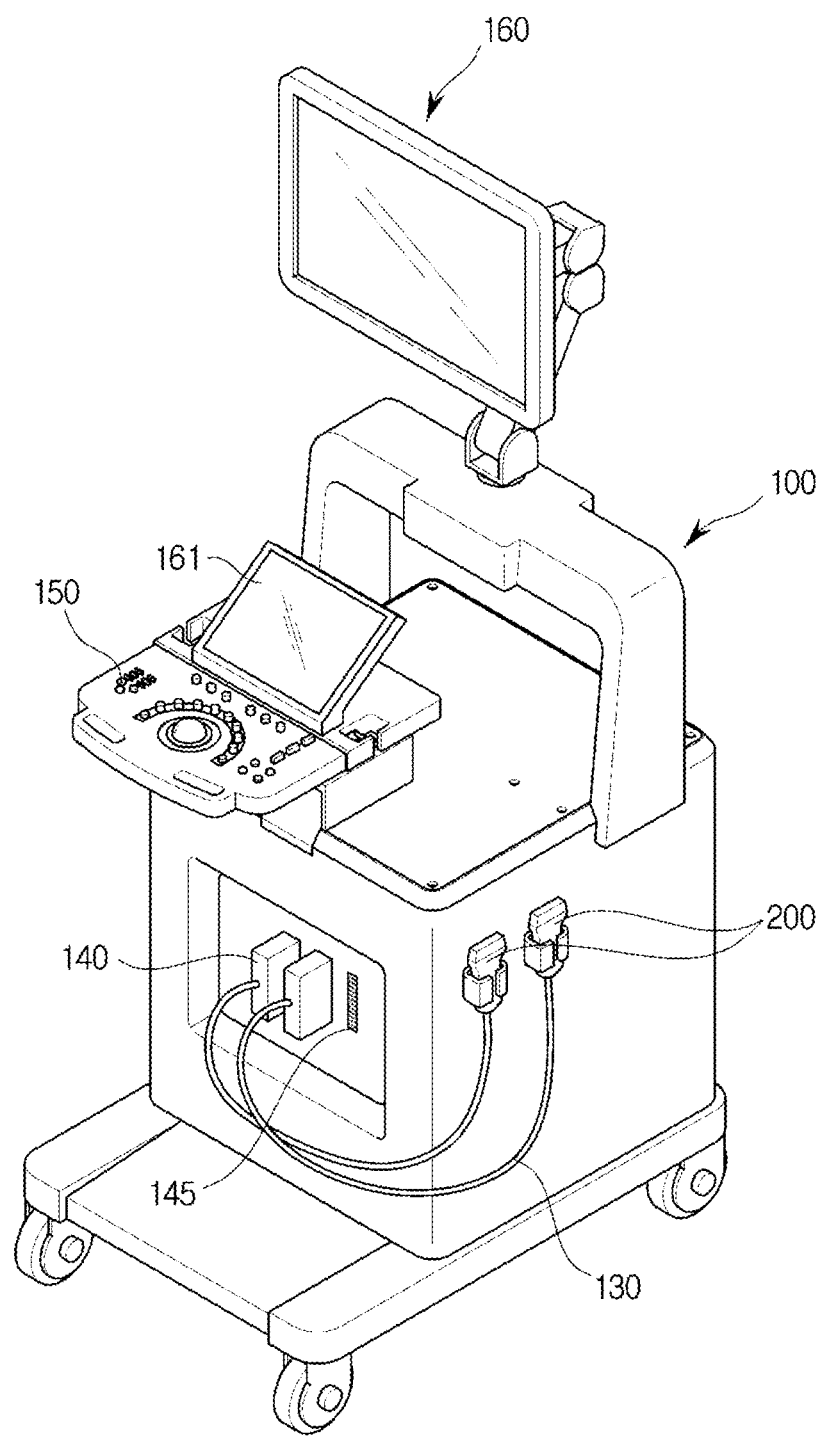
FIG. 1 is a diagram illustrating an exterior of an ultrasound imaging apparatus according to an embodiment.

Advantages and features of the present invention, and methods of achieving the same will be clearly understood with reference to the accompanying drawings and the following detailed embodiments.

Embodiments described in this specification and configurations illustrated in drawings are only exemplary examples of the disclosed invention. It is understood that the invention covers various modifications that can substitute for the embodiments herein and drawings at the time of filing of this application.

An ultrasound imaging apparatus and a method of controlling the same according to embodiments to be described will be described in detail below with reference to the accompanying drawings. The same reference number refers to the same component in the drawings, and redundant descriptions thereof will be omitted.

In this specification, the term "subject" may include a human, an animal, or a part thereof. For example, the subject may include organs such as liver, heart, uterus, brain, breast and abdomen or blood vessels. Also, in this specification, the term "user" refers to a doctor, a nurse, a clinical pathologist, a medical image specialist, or a technician who repairs a medical device, but the present invention is not limited thereto.

The term "ultrasound image" used throughout this specification refers to an image of the subject obtained using an ultrasound, and also may refer to an image of the subject obtained using an X-ray diagnostic apparatus, a computerized tomography (CT) scanner, a magnetic resonance imaging (MRI) apparatus, or a nuclear diagnostic apparatus. Also, a diagnostic apparatus to which technology for the ultrasound imaging apparatus and the method of controlling the same according to the embodiment can be applied or used may broadly include any of an X-ray imaging apparatus, a fluoroscopic X-ray imaging apparatus, a CT scanner, a magnetic resonance imaging (MRI) apparatus, a positron emission tomography apparatus, and an ultrasound imaging apparatus. The ultrasound imaging apparatus will be exemplified in the following embodiments, but the present invention is not limited thereto.

Throughout this specification, when a certain part "includes" a certain component, it means that another component may be further included not excluding another component unless otherwise defined. Moreover, terms described in the specification such as " . . . part," or "module," refer to a unit of processing at least one function or operation, and may be implemented by hardware or software or a combination thereof.

FIG. 1 is a diagram illustrating an exterior of an ultrasound imaging apparatus according to an embodiment.

As illustrated in FIG. 1, the ultrasound imaging apparatus may include a main body 100, and an input unit 150, a display unit 160, a sub display panel 161 and an ultrasound probe 200, which are connected to the main body 100.

Meanwhile, a plurality of casters (not illustrated) may be provided below the main body 100 of the ultrasound imaging apparatus in order to move the ultrasound imaging apparatus. The plurality of casters may enable the ultrasound imaging apparatus to be fixed at a specific location or to move in a specific direction. This ultrasound imaging apparatus is called a cart type ultrasound imaging apparatus.

Also, unlike FIG. 1, the ultrasound imaging apparatus may be a mobile ultrasound imaging apparatus that may be carried when moving in a long distance. In this case, the mobile ultrasound imaging apparatus may have no caster. Examples of the mobile ultrasound imaging apparatus may include a PACS viewer, a smart phone, a laptop computer, a PDA, and a tablet PC, but the present invention is not limited thereto.

The ultrasound probe 200 is a unit that comes in contact with a body surface of the subject, and may transmit and receive an ultrasound to and from the subject. Specifically, the ultrasound probe 200 may generate an ultrasound according to an input pulse, transmit the generated ultrasound into the subject, and receive an echo ultrasound reflected from a specific area inside the subject.

The main body 100 of the ultrasound imaging apparatus may deliver an ultrasound signal to the ultrasound probe 200, receive an echo ultrasound signal from the ultrasound probe 200, and generate of an ultrasound image based thereon.

This generated ultrasound image may be provided to a user through the display unit 160. The user may visually check an ultrasound image of an inside of the subject provided through the display unit 160, and diagnose the subject, that is, a patient.

The display unit 160 may display various UIs related to control of the ultrasound imaging apparatus. The user may check the UI provided through the display unit 160, and input a control command of the ultrasound imaging apparatus or a component of the ultrasound imaging apparatus through the input unit 150.

Also, the display unit 160 may display ultrasound images obtained in an ultrasound diagnostic process. The display unit 160 may be implemented as any known embodiment such as a cathode ray tube (CRT) or a liquid crystal display (LCD), and may also provide a 2D image and a 3D image.

The user may input a control command related to the ultrasound imaging apparatus by touching the display unit 160. The user may also input a touch command for setting a region of interest (ROI) to be observed or diagnosed by the user in an ultrasound image of the subject.

Also, the display unit 160 may display a gain compensation regulating unit configured to compensate for a gain of the ultrasound image. The ultrasound image may have a different definition or brightness of an image quality according to a difference of depth or lateral pixel values. This is because a difference in a degree of the ultrasound signal that is reflected and returned or a time difference is generated according to a depth of the subject. When the ultrasound image is displayed, it is necessary to compensate for such a difference value. There may be several values related to a gain of the ultrasound image. However, in order to describe a gain compensation value according to an embodiment of the disclosed invention, a TGC regulating unit configured to regulate a time gain compensation (TGC) value or an LGC regulating unit configured to regulate a lateral gain compensation (LGC) value will be exemplified. The TGC is a value of the depth, and the LGC is a difference value of left and right pixels. The TGC will be exemplified in embodiments of the disclosed invention. However, the gain compensation value of the ultrasound image is not limited to the TGC or LGC, but various embodiments are available.

According to an embodiment of the disclosed invention, the display unit 160 may display the TGC or LGC regulating unit for a region set as the ROI by the user in the ultrasound image of the subject. That is, no TGC or LGC regulating unit is displayed for a region that is not set as the ROI by the user, the TGC or LGC regulating unit of the ROI is displayed, and thus it is possible to compensate for a gain of the ROI accurately and precisely.

When the user touches the display unit 160 on which the ultrasound image is displayed, the ROI may be set, or when the user touches the TGC regulating unit or the LGC regulating unit of the ROI, the TGC or LGC value may be regulated. The display unit 160 may include a touch panel capable of receiving a touch input by the user. The touch panel may be implemented as a liquid crystal display (LCD) panel, a light emitting diode (LED) panel, an organic light emitting diode (OLED) panel, or the like.

Similar to the display unit 160, the sub display panel 161 can display various UIs related to control of the ultrasound imaging apparatus. The user may check the UI provided through the sub display panel 161, and input a control command of the ultrasound imaging apparatus or a component of the ultrasound imaging apparatus through the input unit 150 or a touch screen of the sub display panel 161.

Also, the sub display panel 161 may display ultrasound images obtained in an ultrasound diagnostic process. The user may input a control command related to the ultrasound imaging apparatus or a command of setting the ROI in the ultrasound image by touching the sub display panel 161. The sub display panel 161 may also display the gain compensation regulating unit configured to compensate for a gain of the ultrasound image, and display the TGC or LGC regulating unit for a region set as the ROI by the user in the ultrasound image of the subject.

The user may set the ROI by touching the sub display panel 161 on which the ultrasound image is displayed, and the user may regulate the TGC or LGC value by touching the TGC regulating unit or the LGC regulating unit of the ROI. The sub display panel 161 may include a touch panel capable of receiving a touch input by the user. The touch panel may be implemented as a liquid crystal display (LCD) panel, a light emitting diode (LED) panel, an organic light emitting diode (OLED) panel, or the like.

The input unit 150 is a unit capable of receiving a command related to an operation of the ultrasound imaging apparatus 100. The user may input commands for starting diagnosis, selecting a region to be diagnosed, selecting a type of diagnosis, selecting a mode of a final output ultrasound image, or the like through the input unit 150.

Also, the user may input a command of setting the ROI in the ultrasound image displayed on the display unit 160 or the sub display panel 161 through the input unit 150. In addition to regulating the value by touching the TGC regulating unit or the LGC regulating unit of the ROI in the ultrasound image displayed on the display unit 160 or the sub display panel 161, the TGC regulating unit or the LGC regulating unit displayed on a screen may be regulated by manipulating a button of the input unit 150. Further, the input unit 150 may receive a storing command for storing the TGC value and LGC value that are regulated with respect to the ROI and a command for loading the stored data. As an embodiment, as illustrated in FIG. 1, the input unit 150 may be positioned above the main body 100. In this case, the input unit 150 may include at least one of a switch, a key, a wheel, a joystick, a trackball, and a knob.

The ultrasound probe 200 may be connected to one end of a cable 130. The other end of the cable 130 may be connected to a male connector 140. The male connector 140 connected to the other end of the cable 130 may be physically connected to a female connector 145 of the main body 100.

According to the above method, the one ultrasound probe 200 may be connected to the one main body 100. Similarly, a plurality of ultrasound probes 200 may also be connected to the one main body 100. For this purpose, a plurality of female connectors may be installed at the main body 100. FIG. 1 exemplifies a case in which the two ultrasound probes 200 are connected to the one main body 100.

Also, unlike FIG. 1, the ultrasound probe 200 may be wirelessly connected to the main body 100. In this case, the ultrasound probe 200 may wirelessly transmit an echo ultrasound signal corresponding to the echo ultrasound received from the subject to the main body 100.

The ultrasound probe 200 may come in contact with the body surface of the subject and transmit and receive an ultrasound to and from the subject. Specifically, the ultrasound probe 200 radiates an ultrasound into the subject according to the ultrasound signal that is an electrical signal provided from the main body 100, collects an echo ultrasound reflected from a specific area inside the subject, and delivers an echo ultrasound signal corresponding thereto to the main body 100.

For this purpose, the ultrasound probe 200 may include a transducer and a multiplexer (MUX) circuit. The transducer may include a plurality of elements that may vibrate and convert an electrical signal into an ultrasound, or convert an ultrasound into an electrical signal. The plurality of elements may be arrayed on one surface of a housing of the ultrasound probe. Specifically, a plurality of transducers may be arranged in a direction parallel with an opening such that an ultrasound may be transmitted and received through the opening provided on the one surface of the housing.

Figure 2:
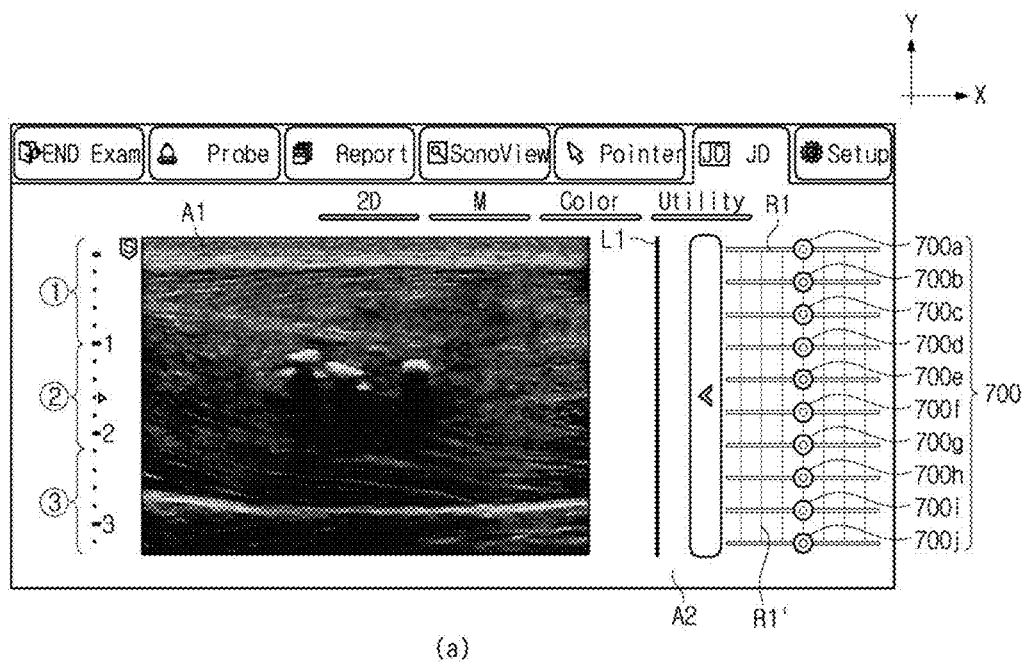
FIG. 2 is a diagram illustrating a case in which a time gain compensation (TGC) value of an ultrasound image is changed according to an embodiment.
Figure 2:
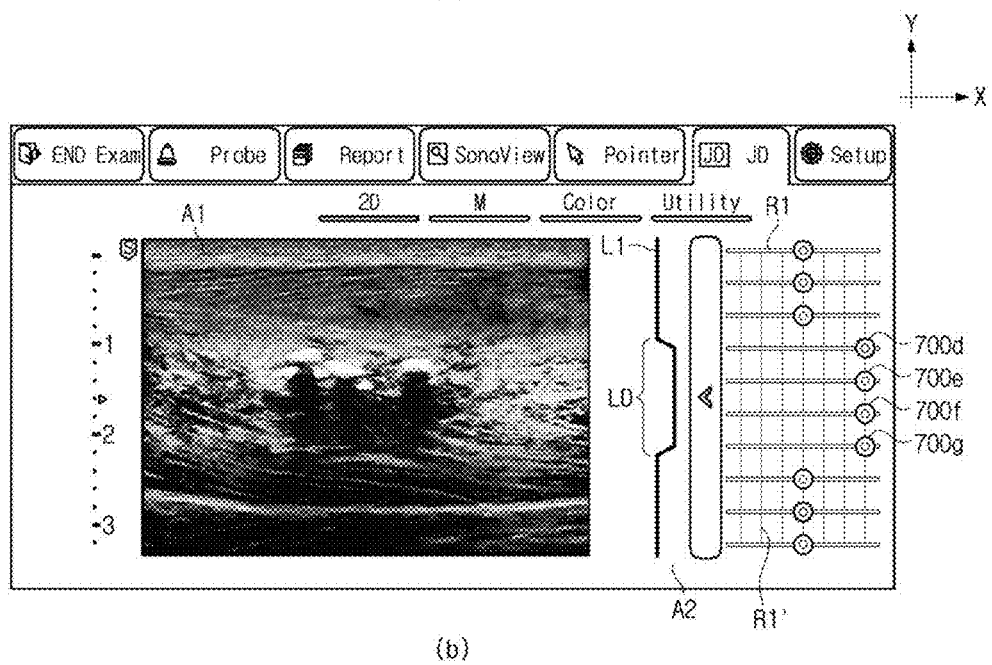

FIG. 2 is a diagram illustrating a case in which a time gain compensation (TGC) value of an ultrasound image is changed according to an embodiment.

Through time gain compensation (TGC), a gain of the depth of the ultrasound image may be regulated. In the ultrasound signal, a signal that arrives at a deeper region of the subject and returns is weaker. Therefore, an ultrasound image of a deep region may be relatively dark and unclear. Therefore, a region that is dark and unclear in the ultrasound image needs to compensate for a gain value by a time difference of the transmitted and received ultrasound signal.

FIG. 2A shows a screen on which an ultrasound image of the subject is displayed on the display unit 160 or the sub display panel 161 according to the embodiment. In this case, the ultrasound image may be displayed on a first region A1 of the display unit 160 or the sub display panel 161. The gain compensation regulating unit including the TGC regulating unit may be displayed on a second region A2.

In the related art, the TGC regulating unit includes a physical button or a control panel in the form of analog. However, the recent TGC regulating unit may be displayed in the form of digital on the display panel as described above.

As illustrated in FIG. 2, the display unit 160 or the sub display panel 161 may display a TGC regulating object 700 and a TGC regulating line L1 on the second region A2 as the TGC regulating unit. The TGC regulating object 700 may include a plurality of objects 700a, 700b, 700c, 700d, 700e, 700f, 700g, 700h, 700i, and 700j. While 10 TGC regulating objects are illustrated in FIG. 2, the number or shapes of the objects are not limited, but various embodiments are available. The plurality of TGC regulating objects 700 may be displayed on a depth reference line R1 in an x axis direction that indicates a level of a depth of the ultrasound image. That is, as illustrated in FIG. 2, the 10 TGC regulating objects 700 may be displayed on the 10 depth reference lines R1. In this case, a level value of the depth of the ultrasound image displayed on the first region A1 may be divided into 10 steps of the depth reference lines R1. The number of depth reference lines R1 and steps thereof are not limited thereto, but various embodiments are available according to settings by the user. In general, as a TGC value of the ultrasound image, a default setting value (an initial setting value) may be set when the ultrasound imaging apparatus 100 is designed. That is, the TGC value may be set such that the ultrasound image can be expressed uniformly at a sufficient brightness. According to a state or conditions of the subject when such a TGC value is provided, the ultrasound image may have different brightness. Further, the user may regulate the TGC value in order to view a brighter or darker ultrasound image.

Also, when the TGC value of the ultrasound image displayed on the first region A1 is regulated, a TGC level reference line R1' in a Y axis direction may be displayed as a reference of the regulated TGC value. The TGC level reference line R1' represents a regulating degree of the TGC value with respect to the Y axis direction, and the number and steps thereof are not limited, but may be changed according to a setting value. Therefore, when the TGC regulating object 700 is positioned in the very left, an ultrasound image of a region regulated by the object may be darkest and when the TGC regulating object 700 is positioned in the very right, an ultrasound image of a region regulated by the object may be brightest.

The TGC regulating unit displayed on the second region A2 may include the TGC regulating line L1 in addition to the TGC regulating object 700. Unlike the TGC regulating object 700 that is fragmentarily divided and displayed according to a depth of the ultrasound image, the TGC regulating line L1 may consider the TGC regulating value of a continuous depth. The TGC regulating line L1 may be displayed in linkage with the TGC regulating object 700. When a position of the TGC regulating object 700 is changed, a form of the TGC regulating line L1 may be changed accordingly. As will be described below, at least any of the TGC regulating object 700 and the TGC regulating line L1 may be displayed on the second region A2 of the display unit 160 or the sub display panel 161. The user may regulate the TGC of the ultrasound image by touching the TGC regulating object 700. When a position of the TGC regulating object 700 is changed, the TGC regulating line L1 may be changed accordingly. Also, when only the TGC regulating line L1 is displayed on the second region A2, the user may touch the TGC regulating line L1 and regulate the TGC of the ultrasound image.

FIG. 2A shows a case in which the ultrasound image of the subject is displayed on the first region A1 of the display unit 160 or the sub display panel 161 before the TGC value is regulated. As illustrated in FIG. 2A, when the displayed ultrasound image is divided into a region ①, a region ② and a region ③, a depth of the ultrasound image increases from the region ① to region ③. In this case, as described above, when the user wants to view the brighter ultrasound image of the subject, a TGC value of the region ② in which the subject is positioned needs to be regulated.

FIG. 2B shows an image in which a TGC value of the region ② of the ultrasound image displayed in FIG. 2A is regulated. As shown in FIG. 2B, it can be understood that the TGC value of the region ② of the ultrasound image is regulated and an ultrasound image corresponding to the region ② becomes brighter. The user may regulate the TGC value of the region ① by regulating the objects 700d, 700e, 700f, and 700g corresponding to the region ② among the objects of the TGC regulating object 700 to be positioned further to the right side than the other objects 700a, 700b, 700c, 700h, 700i, and 700j. When the TGC regulating object 700 is regulated, the TGC regulating line L1 may be displayed such that a part LD corresponding to the region ② is inclined to the right side. The user may input a control command through the input unit 150 or directly touch the display unit 160 or the sub display panel 161 to regulate the TGC regulating object 700.

Figure 3:
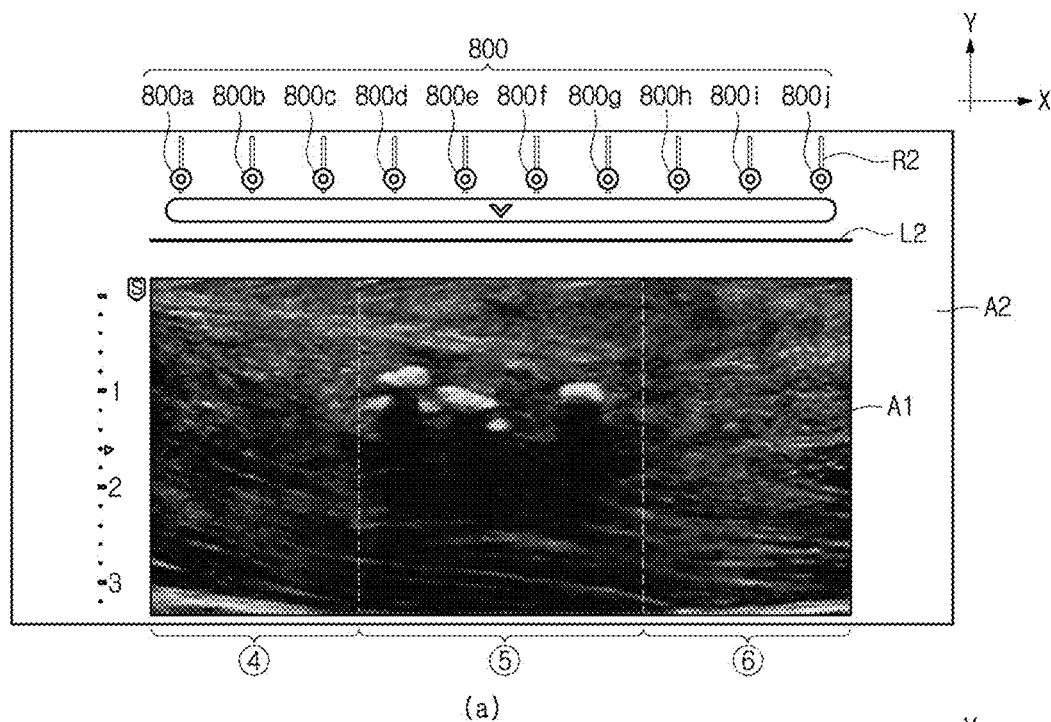
FIG. 3 is a diagram illustrating a case in which a lateral gain compensation (LGC) value of an ultrasound image is changed according to an embodiment.
Figure 3:
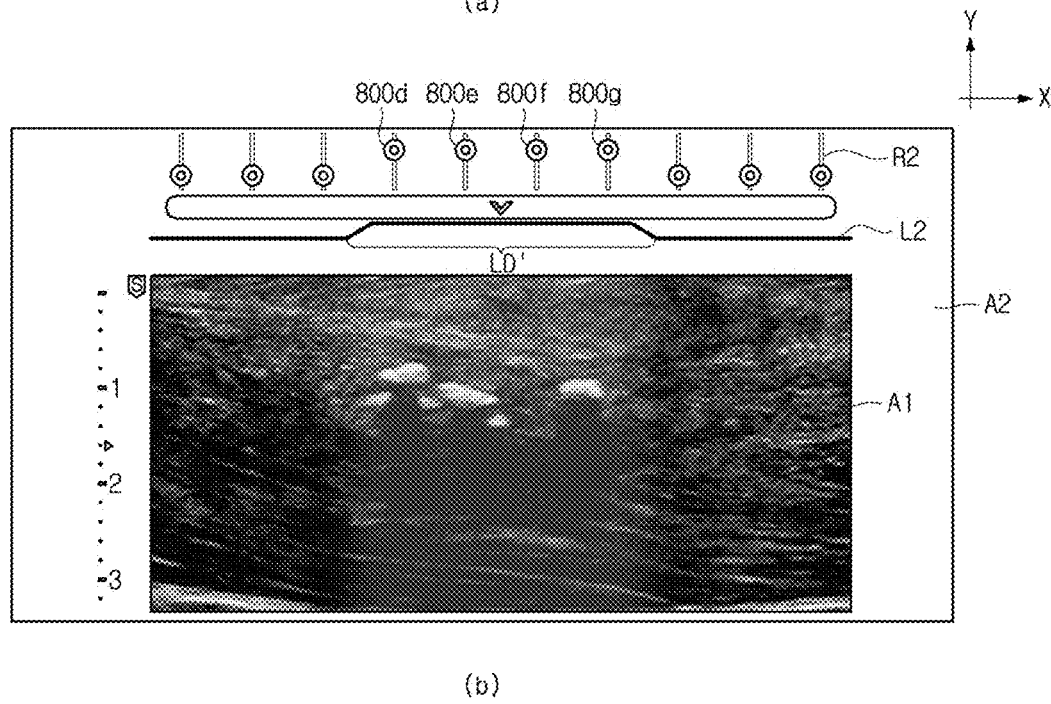

FIG. 3 is a diagram illustrating a case in which a lateral gain compensation (LGC) value of an ultrasound image is changed according to an embodiment.

Through lateral gain compensation (LGC), a gain of a lateral side of the ultrasound image is regulated. Similar to the TGC value, as the LGC value of the ultrasound image, a default setting value (an initial setting value) may be set when the ultrasound imaging apparatus 100 is designed. According to a state or conditions of the subject when the LGC value is set as the default setting value, the ultrasound image may have different lateral brightness. Further, the user may regulate the LGC value in order to view a brighter or darker ultrasound image in a lateral direction.

Similar to FIG. 2, FIG. 3A shows a screen on which the ultrasound image of the subject is displayed on the display unit 160 or the sub display panel 161 according to the embodiment. In this case, the ultrasound image may be displayed on the first region A1 of the display unit 160 or the sub display panel 161. The gain compensation regulating unit including the LGC regulating unit may be displayed on the second region A2.

In the related art, the LGC regulating unit includes a physical button or a control panel in the form of analog. However, the recent LGC regulating unit may be displayed in the form of digital on the display panel as described above.

As illustrated in FIG. 3, the display unit 160 or the sub display panel 161 may display an LGC regulating object 800 and an LGC regulating line L2 as the LGC regulating unit on the second region A2. The LGC regulating object 800 may include a plurality of objects 800a, 800b, 800c, 800d, 800e, 800f, 800g, 800h, 800i, and 800j. While 10 LGC regulating objects are illustrated in FIG. 3, the number or shapes of the objects are not limited, but various embodiments are available. The plurality of LGC regulating objects 800 may be displayed on a brightness reference line R2 in a y axis direction that indicates a level of lateral brightness of the ultrasound image. That is, as illustrated in FIG. 3, the 10 LGC regulating objects 800 may be displayed on 10 brightness reference lines R2. In this case, a level value of the lateral brightness of the ultrasound image displayed on the first region A1 may be divided into 10 steps of the brightness reference lines R2. According to the left and right side of the brightness reference line R2, the ultrasound image may be displayed in different brightness. The number or steps of the brightness reference lines R2 are not limited, but various embodiments are available according to settings by the user.

Also, although not illustrated, an LGC reference line (not illustrated) in an x axis direction may be displayed together with the brightness reference line R2. That is, the LGC reference line represents a regulating degree of the LGC value with respect to the y axis direction. Therefore, when the LGC regulating object 800 is positioned at the very bottom, an ultrasound image of a region regulated by the object may be darkest, and when the LGC regulating object 800 is positioned at the very top, an ultrasound image of a region regulated by the object may be brightest. The number and steps of such LGC reference lines are not limited, but various embodiments are available according to settings by the user.

The LGC regulating unit displayed on the second region A2 may include the LGC regulating line L2 in addition to the LGC regulating object 800. Unlike the LGC regulating object 800 that is fragmentarily divided and displayed according to lateral brightness of the ultrasound image, the LGC regulating line L2 may consider the LGC regulating value of continuous lateral brightness. The LGC regulating line L2 may be displayed in linkage with the LGC regulating object 800. When a position of the LGC regulating object 800 is changed, a form of the LGC regulating line L2 may be changed accordingly. Similar to the TGC regulating unit, at least any of the LGC regulating object 800 and the LGC regulating line L2 may be displayed on the second region A2 of the display unit 160 or the sub display panel 161. The user may regulate the LGC of the ultrasound image by touching the LGC regulating object 800. When a position of the LGC regulating object 800 is changed, the LGC regulating line L2 may be changed accordingly. Also, when only the LGC regulating line L2 is displayed on the second region A2, the user may touch the LGC regulating line L2 and regulate the LGC of the ultrasound image.

FIG. 3A shows a case in which the ultrasound image of the subject is displayed on the first region A1 of the display unit 160 or the sub display panel 161 before the LGC value is regulated. As illustrated in FIG. 3A, when the displayed ultrasound image is divided into a region ④, a region ⑤ and a region ⑥, since brightness of the region ⑤ in which the subject is positioned is low, the LGC value of the region ⑤ needs to be regulated.

FIG. 3B illustrates an image in which the LGC value of the region ⑤ of the ultrasound image displayed in FIG. 3A is regulated. As illustrated in FIG. 3B, it can be understood that the LGC value of the region ⑤ of the ultrasound image is regulated and brightness of the ultrasound image corresponding to the region ⑤ increases. The user may regulate the LGC value of the region ⑤ by regulating the objects 800*d*, 800*e*, 800*f*, and 800*g* corresponding to the region ⑤ among the objects of the LGC regulating object 800 to be positioned above the other objects 800*a*, 800*b*, 800*c*, 800*h*, 800*i*, and 800*j*. According to the regulation of the LGC regulating object 800, the LGC regulating line L2 may also be displayed with a part LD' corresponding to the region ⑤ moved upward. The user may input a control command through the input unit 150 or directly touch the display unit 160 or the sub display panel 161 to regulate the LGC regulating object 800.

Figure 4:
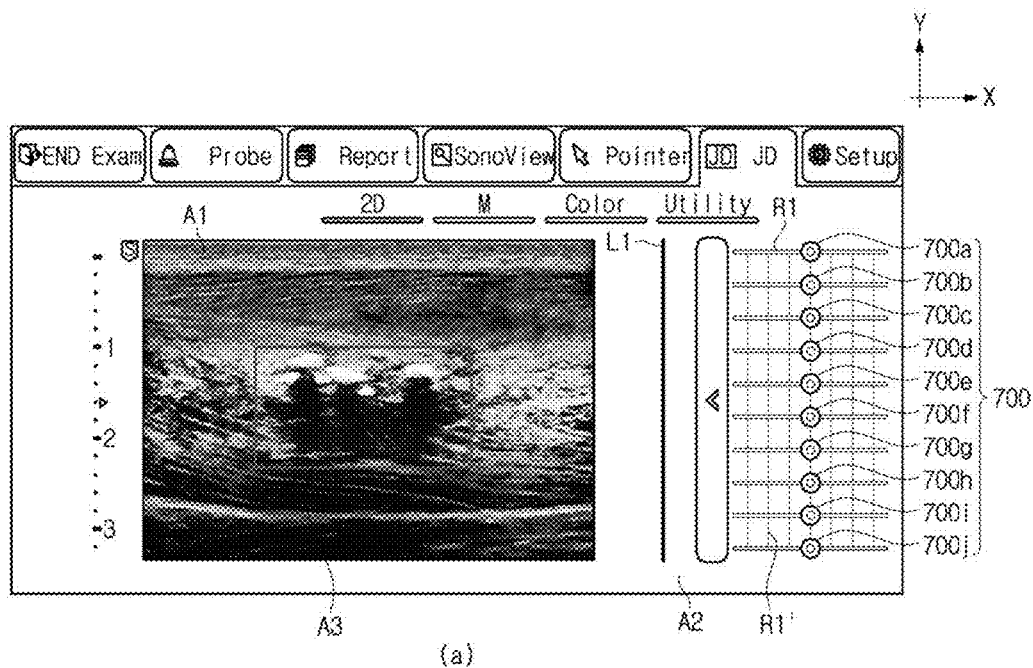
FIG. 4 is a diagram illustrating a display mode of a TGC regulating unit when a region of interest (ROI) in an ultrasound image is set in the related art.
Figure 4:
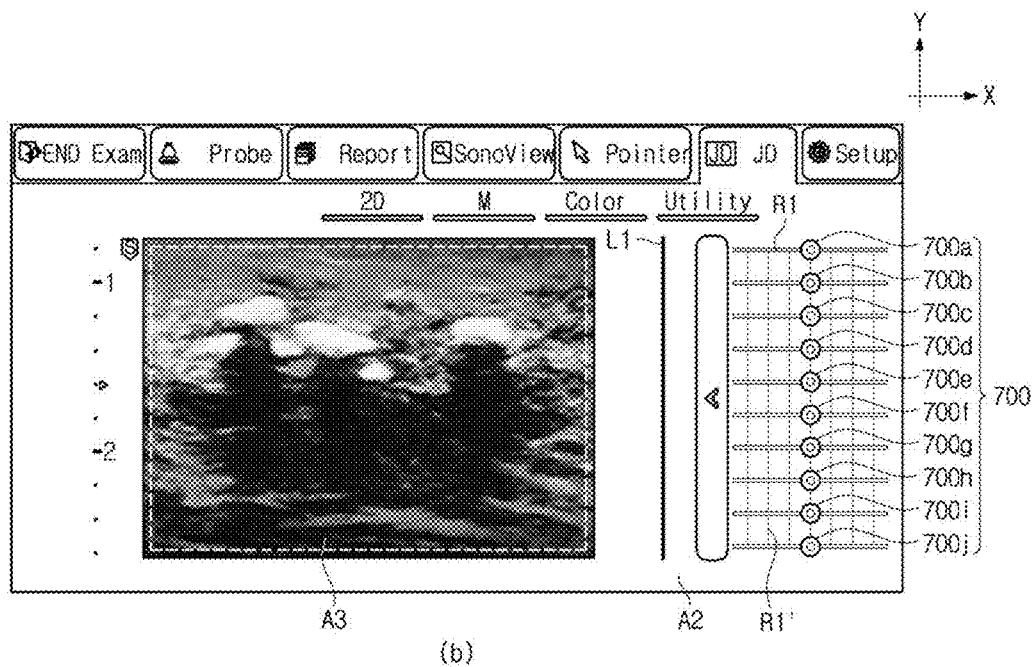

FIG. 4 is a diagram illustrating a display mode of a TGC regulating unit when a region of interest (ROI) in an ultrasound image is set in the related art.

FIG. 4A shows a screen of the display unit 160 when a region of interest (ROI) A3 of the subject in the ultrasound image displayed on the first region A1 is set and displayed. When the ROI in the ultrasound image is set, a setting region or a setting range is not limited, and the set ROI may be enlarged or reduced and then displayed. Also, the set ROI may be moved and rotated, and the ROI itself to be set may be enlarged. The user may input a command for the ROI A3 of the ultrasound image through the input unit 150, or input a touch command of directly setting the ROI A3 of the ultrasound image on the screen of the display unit 160 or the sub display panel 161. When the ROI A3 of the ultrasound image input by the user is enlarged and then displayed, it can be displayed as in FIG. 4B. In this case, an image enlarging technique generally used in the ultrasound imaging apparatus may be used. The image enlarging technique used in the ultrasound imaging apparatus includes a read zoom technique and a write zoom technique.

The read zoom technique is a technique in which an image is frozen, and a specific area in the frozen image is enlarged. When data corresponding to a specific area in image data of one frame stored in a memory is filled in the entire screen again, the enlarged image may be provided. In this case, values of empty pixels that correspond to parts in which data before enlargement and monitor pixels do not match are generally obtained using linear interpolation.

The write zoom technique is a technique in which an array transducer and other parts are designed such that a transceiving scan line denser than a transceiving scan line used in the image may be formed when the ultrasound imaging apparatus is designed, and when an unenlarged image is viewed, the image is composed of only some scan lines (for example, even-numbered scan lines), and the image is enlarged using the entire dense transceiving scan line at a part at which the image is enlarged.

As illustrated in FIG. 4B, even when the ROI A3 of the ultrasound image is enlarged and displayed, the TGC regulating objects 700*a* to 700*j* and the TGC regulating line L1 are displayed to correspond to an entire image before the ROI A3 is enlarged. That is, in FIG. 4B, the TGC regulating objects 700*d*, 700*e*, 700*f*, and 700*g* corresponding to the ROI A3 of the ultrasound image are regulating units necessary for regulating the TGC value of the ROI A3, but the TGC regulating objects 700*a*, 700*b*, 700*c*, 700*h*, 700*i*, and 700*j* corresponding to parts that are not displayed on the screen other than the ROI A3 correspond to objects that have no influence on TGC regulation of the ROI A3. Therefore, only the TGC regulating objects 700*d*, 700*e*, 700*f*, and 700*g* corresponding to the ROI A3 are not displayed. Accordingly, the user may unnecessarily manipulate the TGC regulating objects 700*a*, 700*b*, 700*c*, 700*h*, 700*i*, and 700*j* corresponding to parts other than the ROI A3, and it is difficult to regulate the TGC value of the ROI A3 accurately and precisely.

Figure 5:
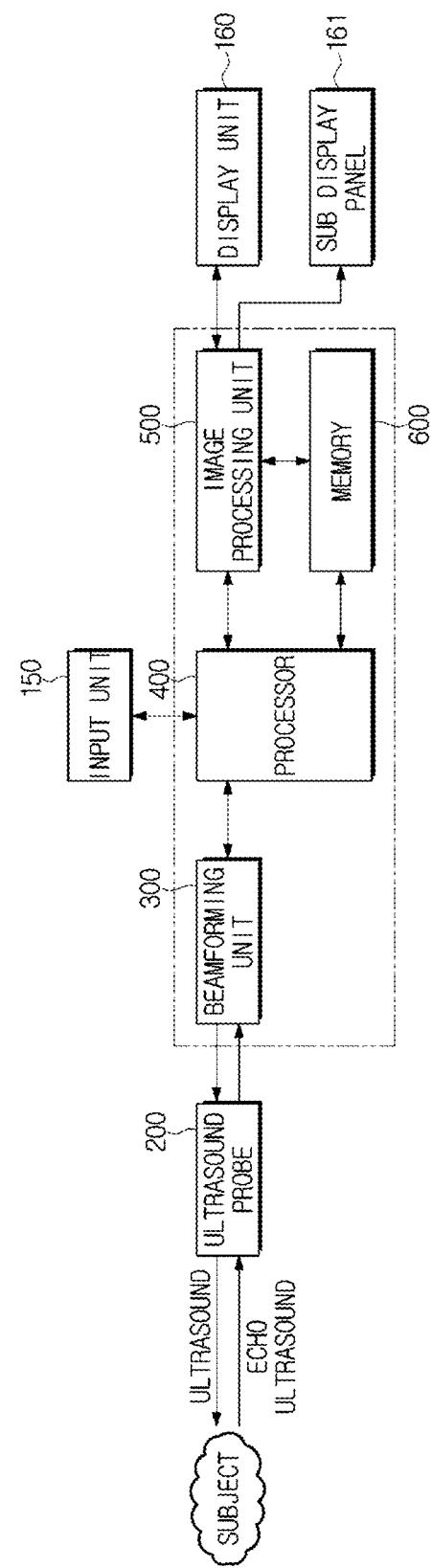
FIG. 5 is a control block diagram illustrating an ultrasound imaging apparatus according to an embodiment.

FIG. 5 is a control block diagram illustrating an ultrasound imaging apparatus according to an embodiment.

As illustrated in FIG. 5, the ultrasound imaging apparatus 100 according to the embodiment may include the input unit 150, the display unit 160, the sub display panel 161, the ultrasound probe 200, a beamforming unit 300, a processor 400, an image processing unit 500, and a memory 600.

The ultrasound probe 200 may be variously implemented in the technological scope in which volume data of the subject is obtained. The ultrasound probe 200 is a unit that comes in contact with the body surface of the subject and can transmit and receive an ultrasound to and from the subject. Specifically, the ultrasound probe 200 generates an ultrasound according to an input pulse, transmits the ultrasound into the subject, and receives an echo ultrasound reflected from a specific area inside the subject.

The beamforming unit 300 may perform beamforming such that ultrasounds transmitted from and received in the ultrasound probe 200 may be focused. The beamforming unit 300 may include a transmitting beamformer (not illustrated) and a receiving beamformer (not illustrated), convert an analog signal and a digital signal, and regulate a time difference of ultrasounds transmitted from at least one transducer or received from at least one transducer. As illustrated in FIG. 1, the beamforming unit 300 may be included in the main body 100 of the ultrasound imaging apparatus, and alternatively, may be included in the ultrasound probe 200 itself to perform its function. When the ultrasound probe is a mobile probe that is connected to the ultrasound imaging apparatus 100 via a wireless communication network, the beamforming unit 300 may be provided in the mobile probe. The beamforming unit 300 may use any one of known beamforming methods, and use combinations of a plurality of methods or selectively use the method.

The processor 400 may receive beamforming data from the beamforming unit 300 and transmit data such that the image processing unit 500 may perform image processing. Also, the processor 400 may store information input from the input unit 150 in the memory 600, and when the user sets the ROI A3 of the ultrasound image according to the embodiment, may perform control such that the ROI A3 is displayed on the display unit 160 or the sub display panel 161. When the user inputs a command of setting the ROI A3 of the ultrasound image, the processor 400 may perform control such that the TGC regulating unit corresponding to the input ROI A3 is displayed. The processor may be implemented as an array of a plurality of logic gates, and may be implemented as a combination of a general purpose microprocessor and a memory in which a program that can be executed in the microprocessor is stored. For example, the image processing unit 500 may be implemented as a general purpose GPU.

The image processing unit 500 may process the beamformed echo ultrasound signal and generate the ultrasound image. The image processing unit 500 may process the echo ultrasound signal according to any one of known image processing methods. For example, the image processing unit 500 may perform time gain compensation (TGC) on the beamformed echo ultrasound signal. Then, the image processing unit 500 may set a dynamic range (DR). After the dynamic range is set, the image processing unit 500 may compress the echo ultrasound signal of the set dynamic range. Finally, the image processing unit 500 may rectify the echo ultrasound signal and then remove noise. The image processing unit 500 may generate the ultrasound image using the echo ultrasound signal processed in this manner. The image processing unit 500 may generate various types of ultrasound images. Examples of the ultrasound image generated by the image processing unit 500 may include an amplitude mode (A-Mode) image, a brightness mode (B-mode) image, a motion mode (M-mode) image, and a Doppler mode image.

According to the embodiment, when the command of setting the ROI A3 of the ultrasound image is input by the user, the image processing unit 500 may generate an image in which a subject image of the set ROI A3 is enlarged or reduced. In this case, the image processing unit 500 may correspond to one or a plurality of processors.

The memory 600 may store information on the ROI A3 of the ultrasound image set according to the embodiment and the TGC regulating unit corresponding to the ROI A3. Specifically, when the ROI A3 set by the user is stored and observation of the ROI A3 is desired again later, data on the ROI A3 may be loaded and a position of the TGC regulating object 700 or a section of the TGC regulating line L1 corresponding to the ROI A3 may be stored.

Also, the user may store information on the ROI A3 of the ultrasound image, the TGC regulating object 700 corresponding to the ROI A3, and optimal TGC regulating values of the ROI A3. The user may easily observe the ROI A3 of the ultrasound image based on the stored data later.

The memory 600 may include, for example, a high-speed random access memory, a magnetic disk, an SRAM, a DRAM, or a ROM, but the present invention is not limited thereto. Also, the memory 600 is detachable from the ultrasound imaging apparatus 100. For example, the memory 600 may include a compact flash (CF) card, a secure digital (SD) card, a smart media (SM) card, a multimedia card (MMC) or a memory stick, but the present invention is not limited thereto. Also, the memory 600 may be provided outside the ultrasound imaging apparatus 100, and transmit or receive data to or from the ultrasound imaging apparatus 100 through a wireless or wired connection.

As described in FIG. 1, the input unit 150 may input a control command of the ultrasound imaging apparatus 100 or a component of the ultrasound imaging apparatus. The user may input a command of setting the ROI in the ultrasound image displayed on the display unit 160 or the sub display panel 161 through the input unit 150. Redundant description thereof will be omitted.

The display unit 160 and the sub display panel 161 may display various UIs related to control of the ultrasound imaging apparatus 100, display ultrasound images obtained in an ultrasound diagnostic process, and provide a 2D image and a 3D image.

The user may input a control command related to the ultrasound imaging apparatus by touching the display unit 160 or the sub display panel 161. The user may also input a touch command of setting the ROI to be observed and diagnosed by the user in the ultrasound image of the subject. Also, the display unit 160 or the sub display panel 161 may display the gain compensation regulating unit configured to compensate for a gain of the ultrasound image. The user may touch the display unit 160 or the sub display panel 161 on which the ultrasound image is displayed to set the ROI, and touch the TGC regulating unit or the LGC regulating unit of the ROI to regulate the TGC or LGC value.

Figure 6:
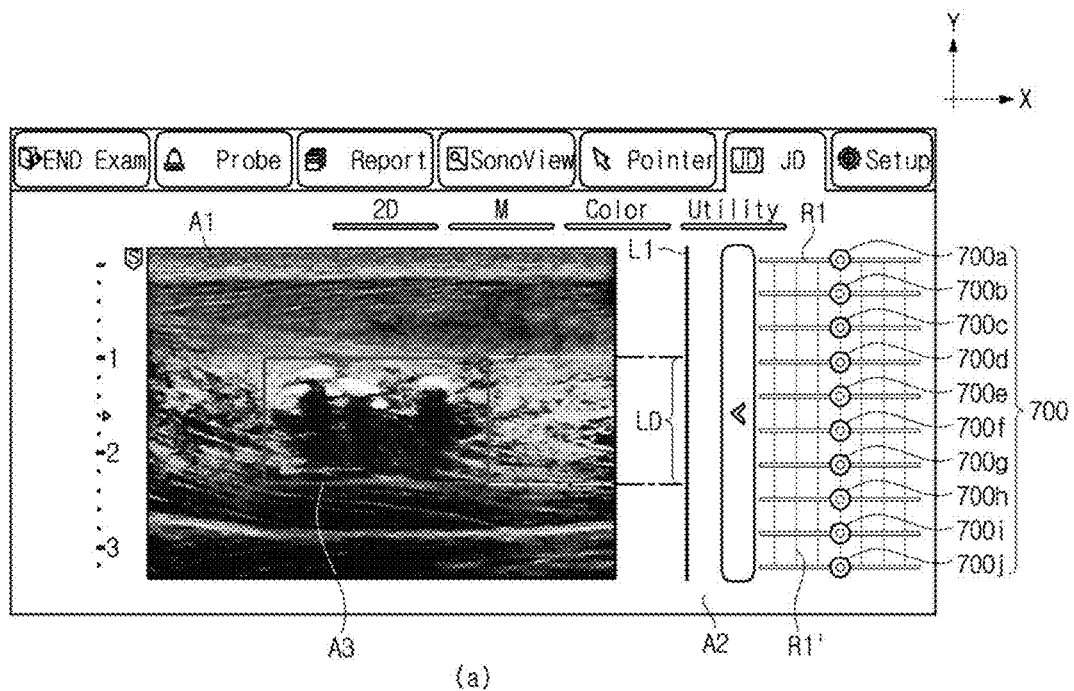
FIG. 6 is a diagram illustrating a display mode of a TGC regulating unit when an ROI in an ultrasound image is set according to an embodiment.
Figure 6:
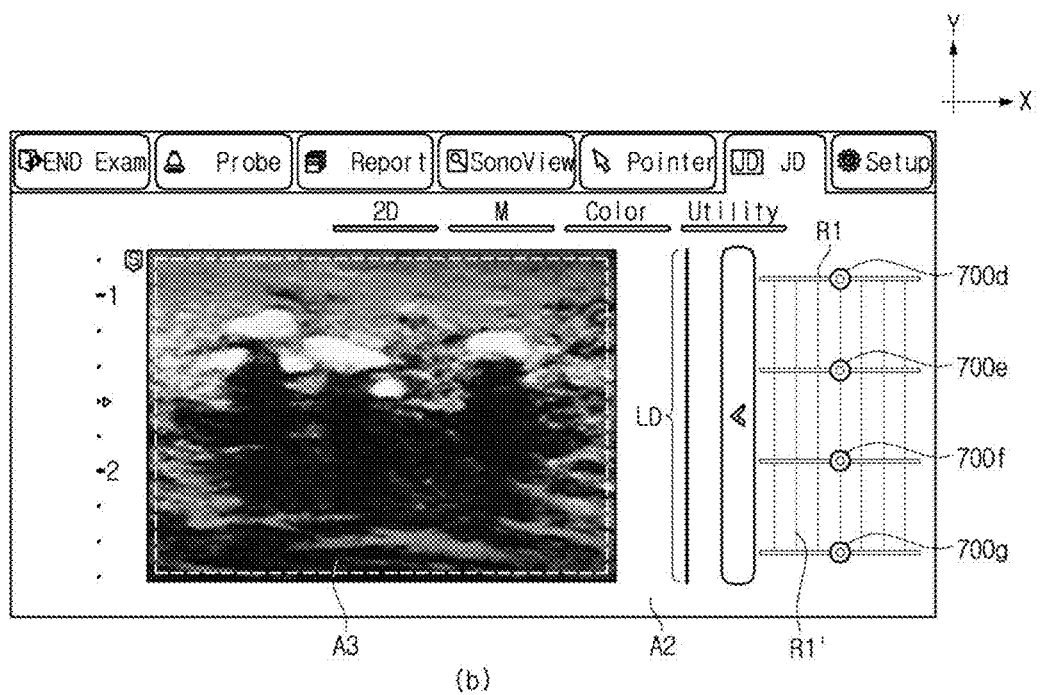

FIG. 6 is a diagram illustrating a display mode of a TGC regulating unit when an ROI in an ultrasound image is set according to an embodiment.

Similar to FIG. 4A, FIG. 6A shows a screen of the display unit 160 when the ROI A3 of the subject in the ultrasound image displayed on the first region A1 is set and displayed.

That is, FIG. 6A shows a screen when only the ROI A3 of the ultrasound image is set before the TGC regulating object 700 is manipulated.

The user may input a command of the ROI A3 of the ultrasound image through the input unit 150, or input a touch command of directly setting the ROI A3 of the ultrasound image on the screen of the display unit 160 or the sub display panel 161.

When the ROI A3 of the ultrasound image input by the user is enlarged and then displayed, it can be displayed as in FIG. 6B. In FIG. 6B, only the TGC regulating objects 700d, 700e, 700f, and 700g corresponding to the ROI A3 of the ultrasound image among the TGC regulating objects 700a to 700j may be displayed. Also, only a TGC regulating line LD corresponding to the ROI A3 may be displayed. In FIG. 6B, the TGC regulating objects 700d, 700e, 700f, and 700g and the TGC regulating line LD corresponding to the ROI A3 are displayed. In order to regulate the TGC value of the ROI A3 on the display screen in FIG. 6B, the user may regulate the TGC regulating objects 700d, 700e, 700f, and 700g. Regulation of the TGC value of the ROI A3 will be described in detail below with reference to FIG. 12. The processor 400 may store the corresponding TGC regulating objects 700a to 700j according to an image depth of the ultrasound image in FIG. 6A before setting of the ROI A3 is input, and display the TGC regulating objects 700d, 700e, 700f, and 700g corresponding to the ROI A3 among the stored TGC regulating objects 700a to 700j when the ROI A3 is set as in FIG. 6B. In FIGS. 6A and 6B, while the four TGC regulating objects 700d, 700e, 700f, and 700g corresponding to the ROI A3 are displayed, the number of corresponding TGC regulating objects 700 and a range thereof may be changed in order to regulate the TGC value of the ROI A3.

The user may regulate the TGC value of the ROI A3 through the TGC regulating objects 700d, 700e, 700f, and 700g corresponding to the ROI A3, and accordingly the TGC regulating line LD corresponding to the ROI A3 may also be changed.

Figure 7:
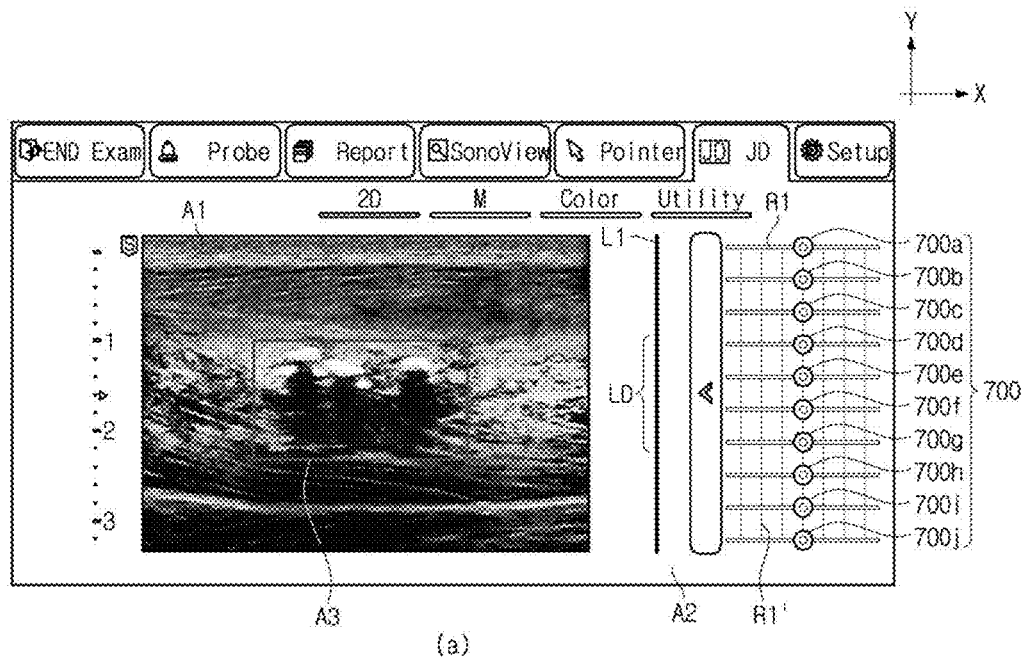
FIG. 7 is a diagram illustrating a case in which a display mode of a TGC regulating unit is emphasized and displayed when an ROI in an ultrasound image is set according to an embodiment.
Figure 7:
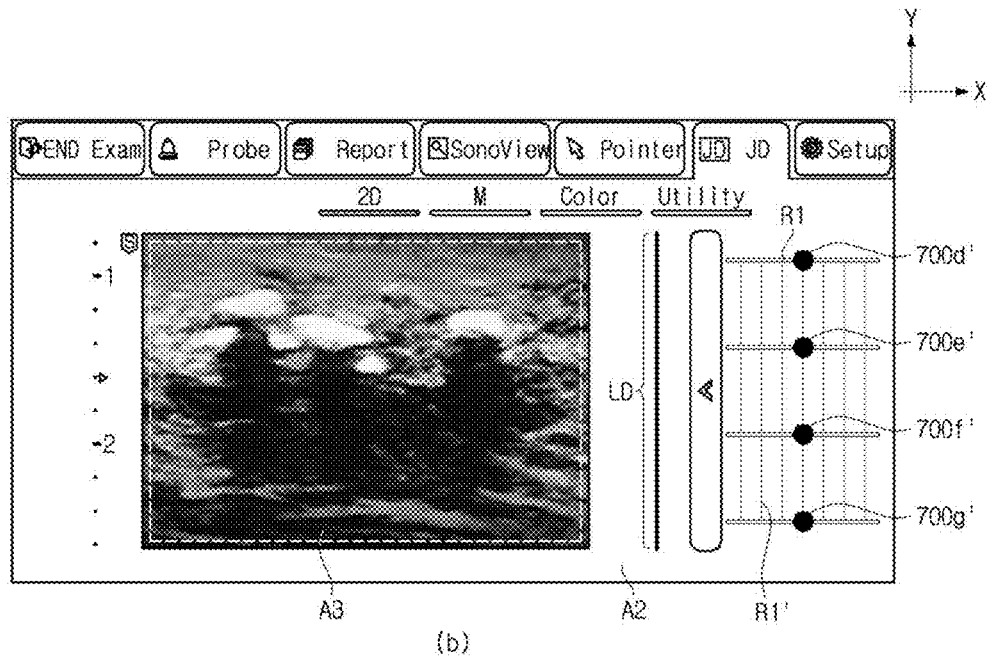

FIG. 7 is a diagram illustrating a case in which a display mode of a TGC regulating unit is emphasized and displayed when an ROI in an ultrasound image is set according to an embodiment.

Similar to FIG. 4A, FIG. 7A shows a screen of the display unit 160 when the ROI A3 of the subject in the ultrasound image displayed on the first region A1 is set and displayed.

When the ROI A3 of the ultrasound image input by the user is enlarged and then displayed, it can be displayed as in FIG. 7B. Only the TGC regulating objects 700d, 700e, 700f, and 700g corresponding to the ROI A3 of the ultrasound image among the TGC regulating objects 700a to 700j may be emphasized and displayed. That is, the TGC regulating objects 700a, 700b, 700c, 700h, 700i, and 700j corresponding to a part other than the ROI A3 and the TGC regulating objects 700d, 700e, 700f, and 700g corresponding to the ROI A3 may be displayed in different forms. As illustrated in FIG. 7B, TGC regulating objects 700d', 700e', 700f', and 700g' corresponding to the ROI A3 may be displayed in colors, sizes, or shapes that are different from the rest TGC regulating objects. Therefore, the user may intuitively recognize the TGC regulating objects 700d', 700e', 700f', and 700g' capable of regulating the TGC value of the ultrasound image set as the ROI A3, and even when a screen on which only the ROI A3 is displayed is enlarged to an entire ultrasound image, it is possible to distinguish the TGC regulating objects corresponding to the ROI A3. The user may regulate the emphasized and displayed TGC regulating objects 700d', 700e', 700f', and 700g' and regulate the TGC value of the ultrasound image of the ROI A3 corresponding thereto accurately and precisely.

A method in which the TGC regulating objects 700d, 700e, 700f, and 700g corresponding to the ROI A3 are emphasized and displayed is not limited to the method in which objects are displayed in different colors, but various embodiments are available.

Figure 8:
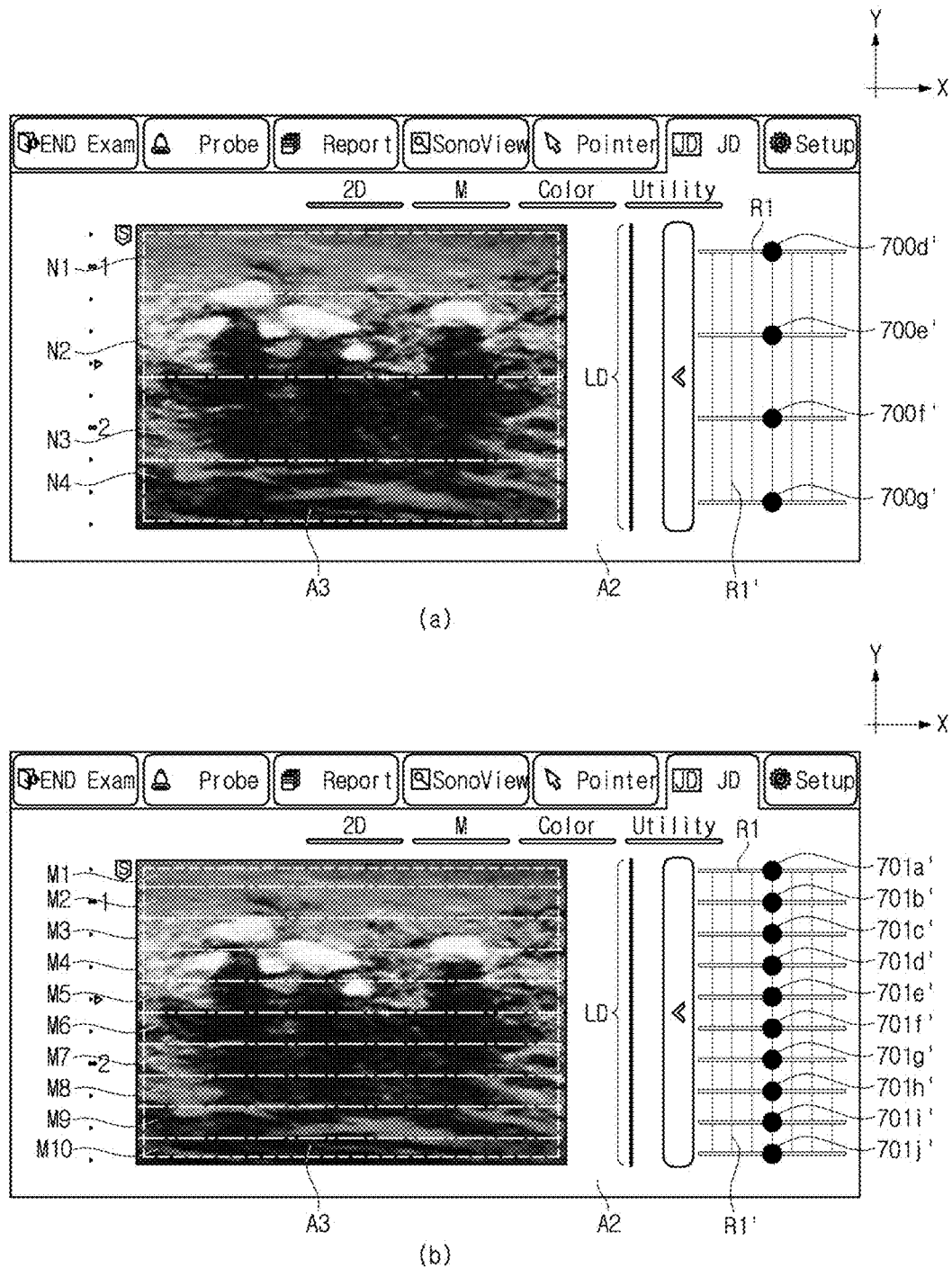
FIG. 8 is a diagram illustrating a case in which a level of a TGC regulating unit corresponding to an ROI in an ultrasound image is increased and displayed according to an embodiment.

FIG. 8 is a diagram illustrating a case in which a level of a TGC regulating unit corresponding to an ROI in an ultrasound image is increased and displayed according to an embodiment.

Similar to FIG. 7B, FIG. 8A shows a screen on which the TGC regulating objects 700d', 700e', 700f', and 700g' corresponding to the ROI A3 of the ultrasound image are emphasized and displayed. As described above, the user may regulate the emphasized and displayed TGC regulating objects 700d', 700e', 700f', and 700g' and regulate the TGC value of the ultrasound image of the ROI A3 corresponding thereto.

In FIG. 8A, the TGC regulating objects corresponding to the ROI A3 are divided into 4 levels and positioned on 4 depth reference lines, respectively. Therefore, in order to regulate the TGC value of the ROI A3, the ROI A3 may be divided into 4 regions, and the TGC value may be regulated by the TGC regulating objects 700d', 700e', 700f', and 700g'. As illustrated in FIG. 8A, lines dividing the ROI A3 into 4 regions may be displayed on the ROI A3 of the ultrasound image. These lines may divide the ROI A3 into 4 regions, N1, N2, N3, and N4. The regions may be displayed to correspond to the TGC regulating objects 700d', 700e', 700f', and 700g', respectively, so that the user may easily regulate the TGC value for each corresponding region. That is, the regions N1, N2, N3, and N4 may correspond to the TGC regulating objects 700d', 700e', 700f', and 700g', respectively, such that the region N1 corresponds to the object 700d' and the region N2 corresponds to the object 700e'. For example, when the object 700d' is regulated, the TGC value of the region N1 may be changed. The number of regions divided in the ROI A3 and shapes thereof and shapes corresponding to the TGC regulating objects 700d', 700e', 700f', and 700g' may be different according to settings.

In order for the user to more finely regulate the TGC than in that of FIG. 8A, the display unit 160 or the sub display panel 161 may display TGC regulating objects 701a' to 701j' divided into 10 levels with respect to the same ROI A3 of the ultrasound image as illustrated in FIG. 8B. It is needless to say that the TGC regulating objects 701a' to 701j' divided into 10 levels may also be emphasized and displayed in different colors, similar to those in FIG. 7 described above.

Display of the TGC regulating objects 701a' to 701j' by further segmenting a section with respect to the same ROI A3 may be performed by a control command input by the user through the input unit 150, or may be implemented by a touch input through the display unit 160 or the sub display panel 161.

The user may regulate the TGC of the ROI A3 of the ultrasound image for each of 10 sections more precisely through the TGC regulating objects 701a' to 701j' divided into 10 levels. That is, as illustrated in FIG. 8B, lines dividing the ROI A3 into 10 regions may be displayed on the ROI A3 of the ultrasound image. These lines may divide the ROI A3 into 10 regions M1, M2, M3, M4, M5, M6, M7, M8, M9, and M10, each of the regions is displayed to correspond to each of the TGC regulating objects 701a', 701b', 701c', 701d', 701e', 701f', 701g', 701h', 701i', and 701j', and thus the user may easily regulate the TGC value for each corresponding region. That is, the regions M1, M2, M3, M4, M5, M6, M7, M8, M9, and M10 may correspond to the TGC regulating objects 701a', 701b', 701c', 701d', 701e', 701f', 701g', 701h', 701i', and 701j', respectively, such that the region M1 corresponds to the object 701a' and the region M2 corresponds to the object 701b'. For example, when the object 701a' is regulated, the TGC value of the region M1 may be changed. The number of regions divided in the ROI A3 and shapes thereof, and shapes corresponding to the TGC regulating objects 701a', 701b', 701c', 701d', 701e', 701f', 701g', 701h', 701i', and 701j' may be different according to settings.

Figure 9:
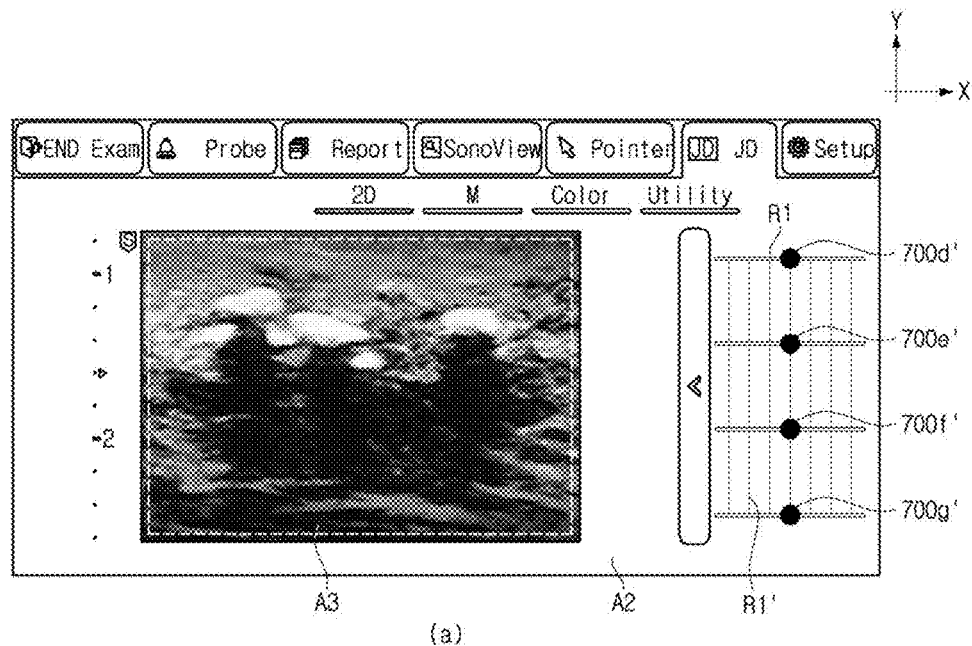
FIG. 9 is a diagram illustrating a case in which only a TGC regulating object or only a TGC regulating line among TGC regulating units corresponding to an ROI in an ultrasound image is displayed according to an embodiment.
Figure 9:
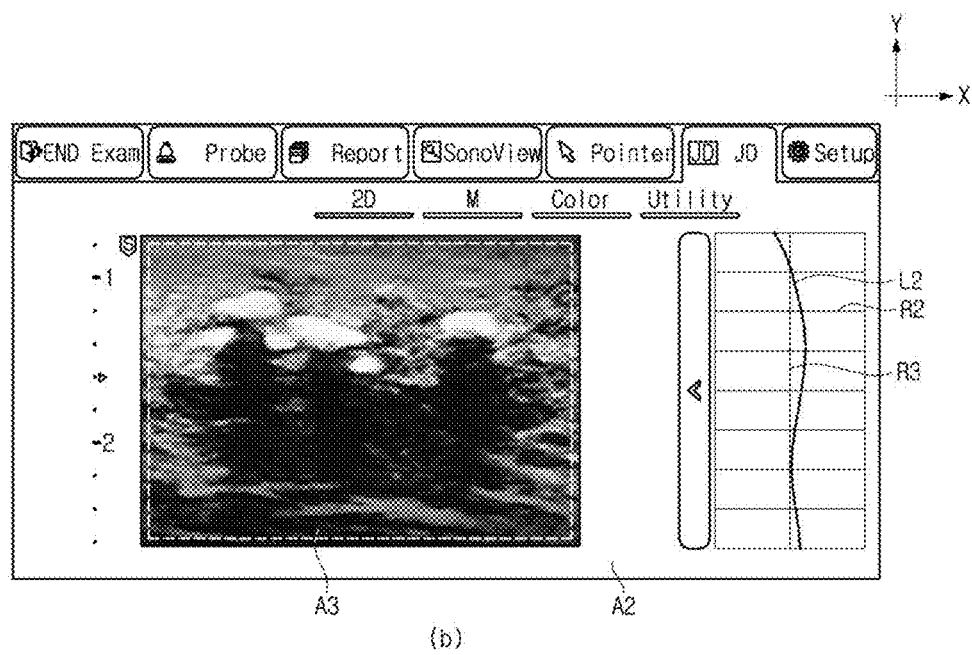

FIG. 9 is a diagram illustrating a case in which only a TGC regulating object or only a TGC regulating line among TGC regulating units corresponding to an ROI in an ultrasound image is displayed according to an embodiment.

Similar to FIG. 7B, FIG. 9A shows a case in which the TGC regulating objects 700d', 700e', 700f', and 700g' corresponding to the ROI A3 of the ultrasound image are emphasized and displayed. However, unlike FIG. 7, only the TGC regulating objects 700d', 700e', 700f', and 700g' corresponding to the ROI A3 are emphasized and displayed, and no TGC regulating line may be displayed.

On the other hand, unlike FIG. 9A, FIG. 9B shows a case in which a TGC regulating line L2 corresponding to the ROI A3 of the ultrasound image is displayed. The TGC regulating line L2 may be displayed along a horizontal direction reference line R2 distinguishing a depth of the ultrasound image and along a vertical direction reference line R3 distinguishing a regulating degree of the TGC value. The user may regulate the TGC regulating line L2 based on the distinguished depth of the ultrasound image along the horizontal direction reference line R2 and regulate the TGC value of the ROI A3.

Figure 10:
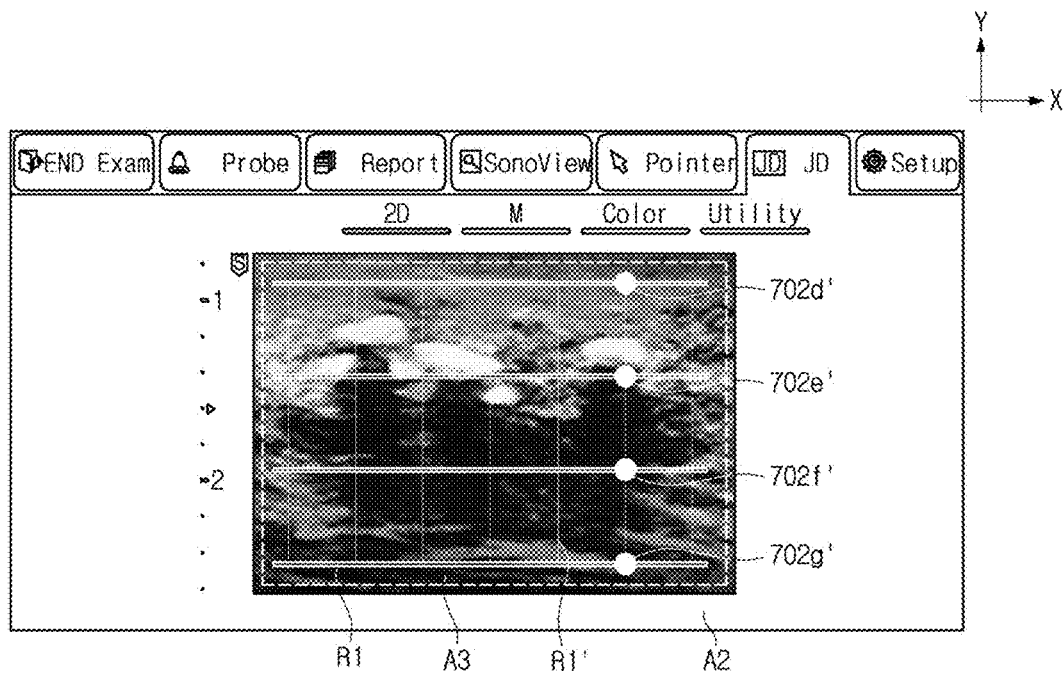
FIG. 10 is a diagram illustrating a case in which a TGC regulating object corresponding to an ROI in an ultrasound image is displayed on an ultrasound image in an overlapping manner according to an embodiment.

FIG. 10 is a diagram illustrating a case in which a TGC regulating object corresponding to an ROI in an ultrasound image is displayed on an ultrasound image in an overlapping manner according to an embodiment.

As illustrated in FIG. 10, the enlarged ROI A3 of the ultrasound image may be displayed on the display unit 160 or the sub display panel 161, and corresponding TGC regulating objects 702d', 702e', 702f', and 702g' may be displayed thereon. That is, unlike display of the TGC regulating objects 700d', 700e', 700f', and 700g' on the second region A2 of the display unit 160 or the sub display panel 161 as illustrated in FIG. 7B, the TGC regulating objects 702d', 702e', 702f', and 702g' may be displayed on the first region A1 on which the ultrasound image is displayed so as to overlap with the ultrasound image. The TGC regulating objects 702d', 702e', 702f', and 702g' may be displayed along the depth reference line R1 and the TGC level reference line R1' of the ultrasound image. The user may regulate the TGC regulating objects 702d', 702e', 702f', and 702g' and regulate the TGC value of the ROI A3. When the user regulates the TGC regulating objects 702d', 702e', 702f', and 702g', the depth reference line R1 and the TGC level reference line R1' may be displayed or removed.

Figure 11A:
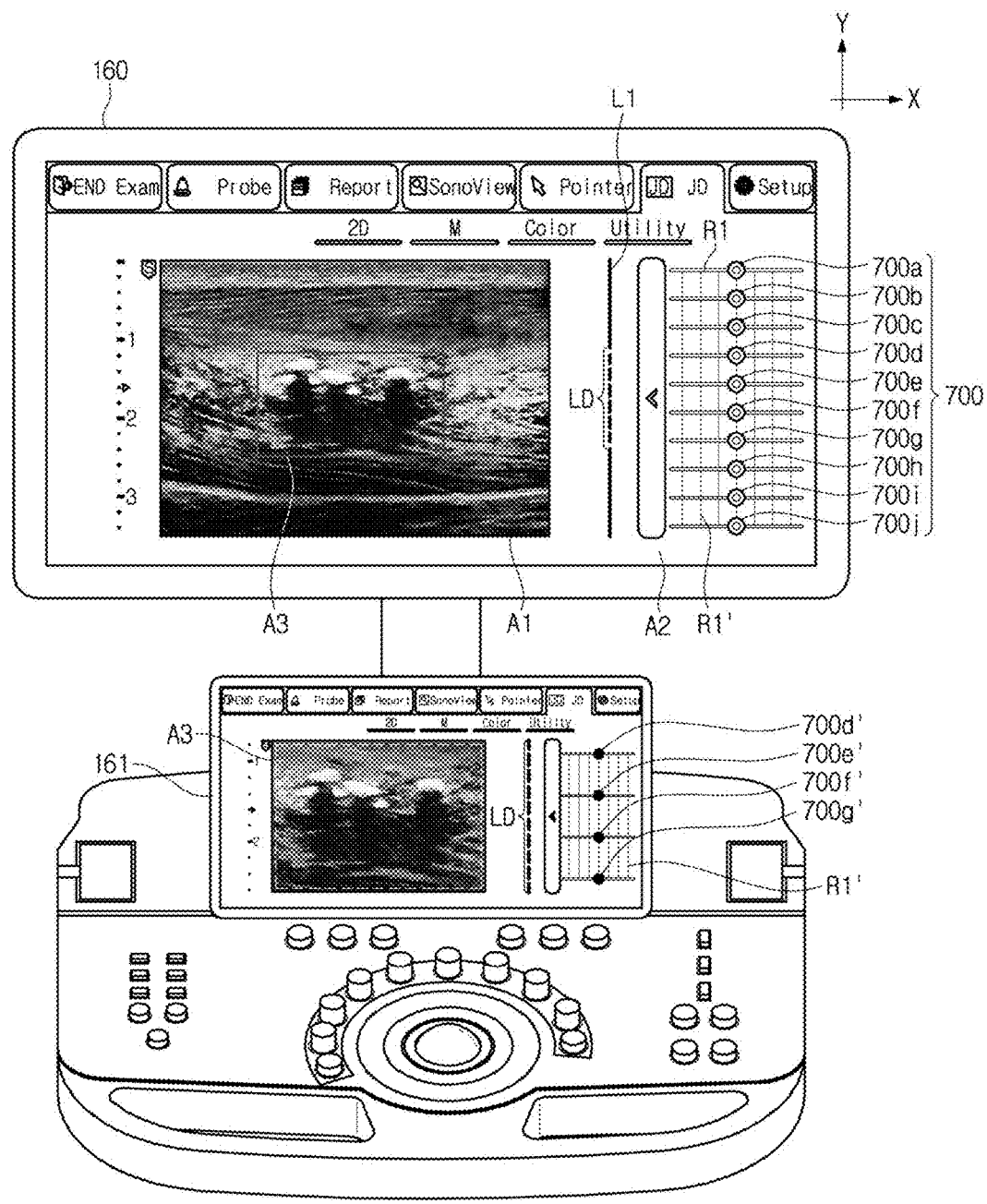
FIG. 11A is a diagram illustrating a case in which an entire ultrasound image and an entire TGC regulating unit are displayed on a display unit and an ROI in an ultrasound image and a TGC regulating unit corresponding thereto are displayed on a sub display panel according to an embodiment.

FIG. 11A is a diagram illustrating a case in which an entire ultrasound image and an entire TGC regulating unit are displayed on a display unit and an ROI in an ultrasound image and a TGC regulating unit corresponding thereto are displayed on a sub display panel according to an embodiment.

As illustrated in FIG. 11A, an ultrasound image may be displayed on the display unit 160 and the sub display panel 161 of the ultrasound imaging apparatus illustrated in FIG. 1. In this case, similar to FIG. 4A, on the display unit 160, an entire ultrasound image of the subject may be displayed on the first region A1, and the TGC regulating object 700 and the TGC regulating line L1 may be displayed on the second region A2.

When the user sets the ROI A3 of the ultrasound image displayed on the display unit 160, the ROI A3 may be displayed on the sub display panel 161. Also, the TGC regulating objects 700d', 700e', 700f', and 700g' and the TGC regulating line LD corresponding to the ROI A3 of the ultrasound image may be displayed on the sub display panel 161. In this case, the TGC regulating line LD corresponding to the ROI A3 may be distinguished from the TGC regulating line L1 and then displayed, and may be displayed with dotted lines as illustrated in FIG. 11A, or displayed in different colors. Screens of the ultrasound image and the TGC regulating unit displayed in FIG. 11A are the same as those in FIGS. 7A and 7B. However, in FIG. 7, the ultrasound image before the ROI A3 is set, the ultrasound image after the ROI A3 is set and the TGC regulating unit corresponding thereto are displayed on each of the display unit 160 and the sub display panel 161. Alternatively, in FIG. 11A, the ultrasound image before the ROI A3 is set may be displayed on the display unit 160, and the set ROI A3 and the TGC regulating unit corresponding thereto may be displayed on the sub display panel 161.

The user may simultaneously view an entire screen of the ultrasound image and the entire TGC regulating unit displayed on the display unit 160 and the ROI A3 of the ultrasound image and the TGC regulating unit corresponding thereto displayed on the sub display panel 161, and may also input a control command of each ultrasound image screen at the same time. It is needless to say that, as described in FIG. 9, only the TGC regulating objects 700d', 700e', 700f', and 700g' corresponding to the ROI A3 may be displayed on the sub display panel 161, and only the TGC regulating line LD corresponding to the ROI A3 may be displayed thereon. The processor 400 may perform control such that the entire ultrasound image and the TGC regulating unit corresponding thereto may be displayed on the display unit 160 based on the control command of setting the ROI A3 input through the input unit 150, the display unit 160 or the sub display panel 161, and perform control such that the ROI A3 of the ultrasound image and the TGC regulating unit corresponding thereto may be displayed on the sub display panel 161.

Figure 11B:
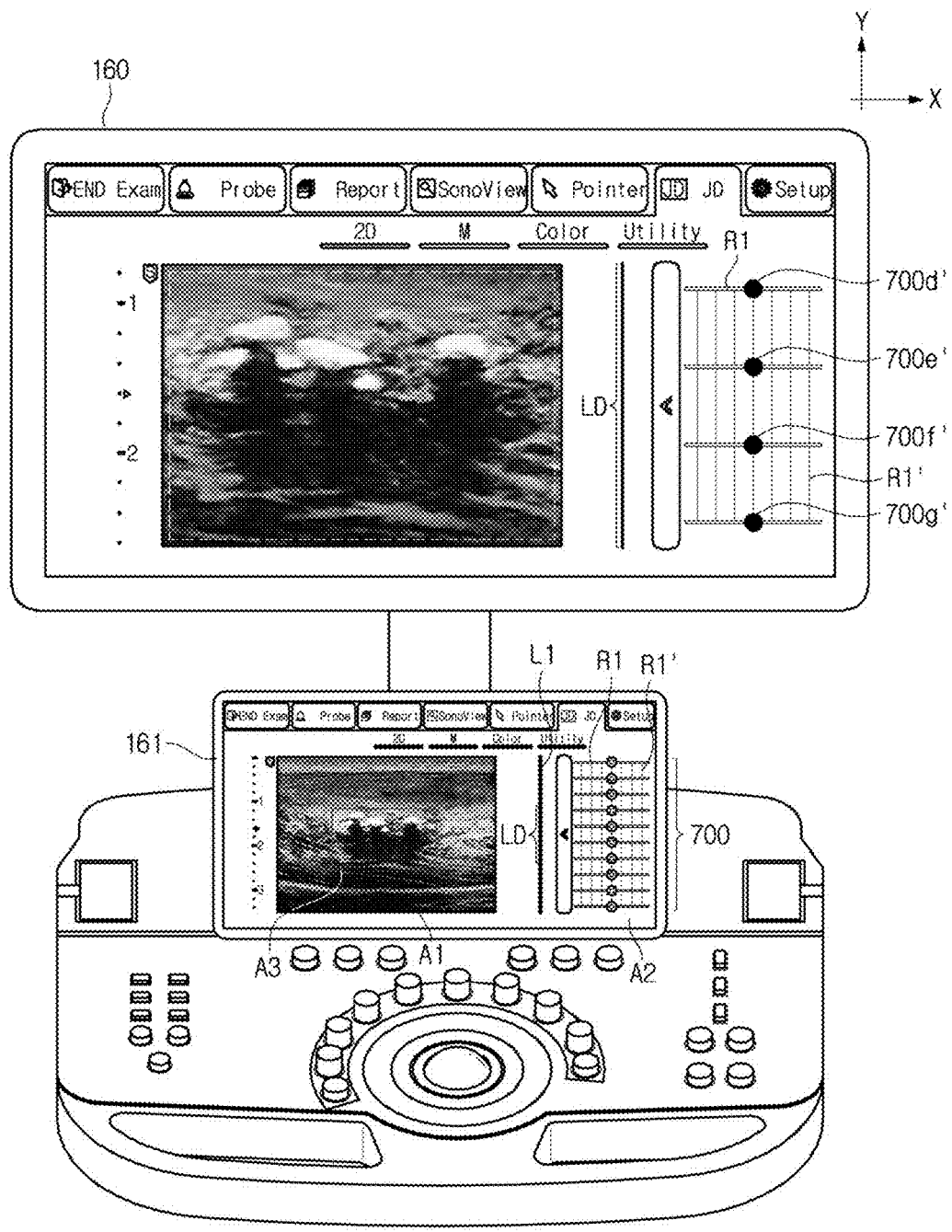
FIG. 11B is a diagram illustrating a case in which an ROI in an ultrasound image and a TGC regulating unit corresponding thereto are displayed on a display unit, and an entire ultrasound image and an entire TGC regulating unit are displayed on a sub display panel according to an embodiment.

FIG. 11B is a diagram illustrating a case in which an ROI in an ultrasound image and a TGC regulating unit corresponding thereto are displayed on a display unit, and an entire ultrasound image and an entire TGC regulating unit are displayed on a sub display panel according to an embodiment.

As illustrated in FIG. 11B, unlike FIG. 11A, on the sub display panel 161, an entire ultrasound image of the subject, the TGC regulating object 700 and the TGC regulating line L1 may be displayed. On the display unit 160, the ROI A3 of the ultrasound image may be displayed and the TGC regulating objects 700d', 700e', 700f', and 700g' and the TGC regulating line LD corresponding to the ROI A3 may be displayed. That is, the user may perform control such that the ROI A3 of the ultrasound image and the TGC regulating unit corresponding thereto displayed on the sub display panel 161 in FIG. 11A are displayed on the display unit 160, and regulate the TGC value of the ROI A3 that is displayed largely on the display unit 160. Similar to FIG. 11A, the TGC regulating line LD corresponding to the ROI A3 may be distinguished from the TGC regulating line L1 and then displayed, and may be displayed with dotted lines as illustrated in FIG. 11B, or displayed in different colors.

Figure 11C:
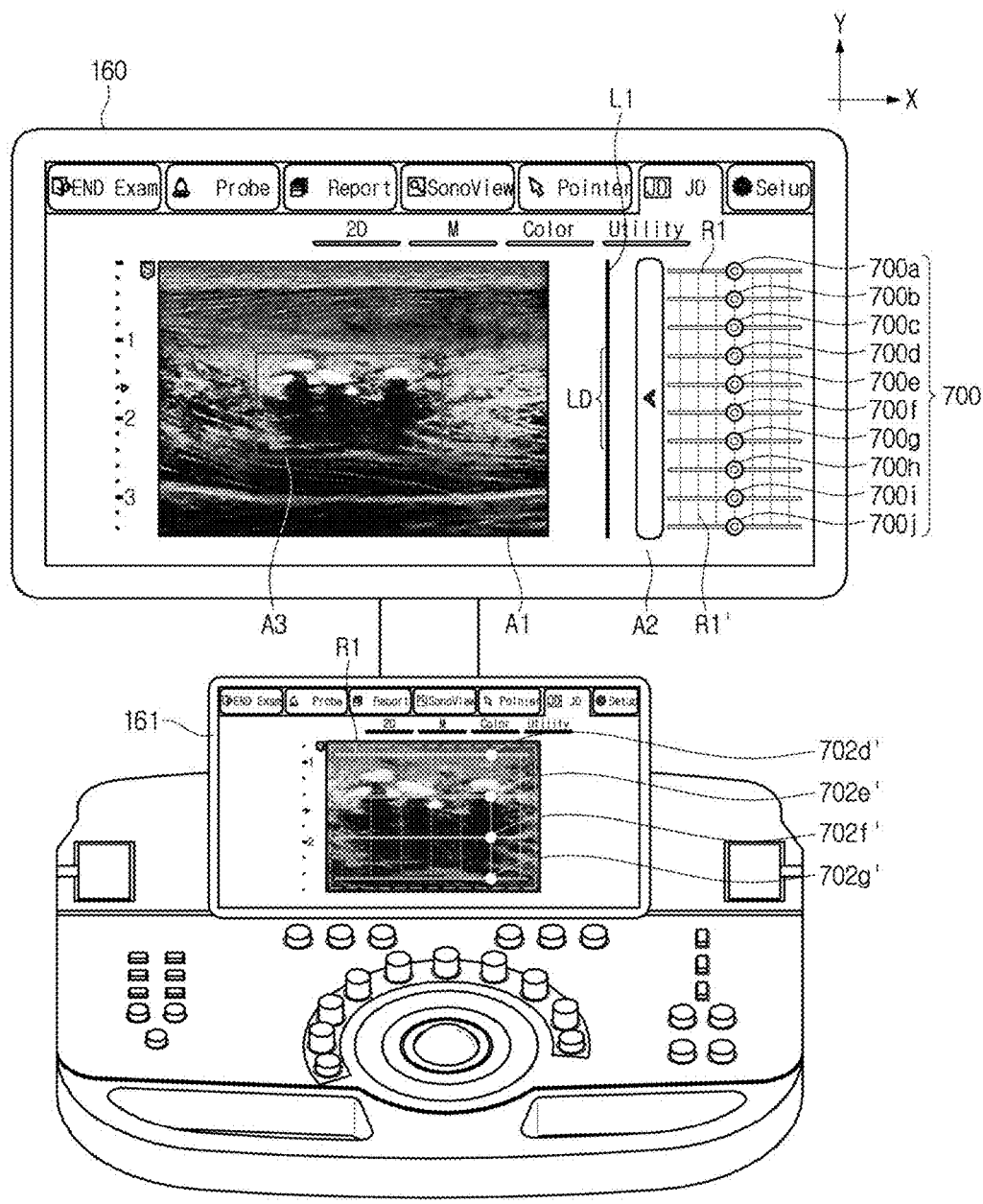
FIG. 11C is a diagram illustrating a case in which an entire ultrasound image and an entire TGC regulating unit are displayed on a display unit and a TGC regulating object corresponding to an ROI in an ultrasound image is displayed on an ultrasound image in an overlapping manner on a sub display panel according to an embodiment.

FIG. 11C is a diagram illustrating a case in which an entire ultrasound image and an entire TGC regulating unit are displayed on a display unit and a TGC regulating object corresponding to an ROI in an ultrasound image is displayed on an ultrasound image in an overlapping manner on a sub display panel according to an embodiment.

As illustrated in FIG. 11C, similar to FIG. 11A, on the display unit 160, an entire ultrasound image of the subject may be displayed on the first region A1, and the TGC regulating object 700 and the TGC regulating line L1 may be displayed on the second region A2. Since this has been described with reference to FIG. 11A to FIG. 11B, redundant descriptions thereof will be omitted.

Similar to description in FIG. 10, the enlarged ROI A3 of the ultrasound image may be displayed on the sub display panel 161, and the TGC regulating objects 702d', 702e', 702f', and 702g' corresponding to the ROI may be displayed thereon. The TGC regulating objects 702d', 702e', 702f', and 702g' may be displayed along the depth reference line R1 of the ultrasound image, and the user may regulate the TGC regulating objects 702d', 702e', 702f', and 702g' and regulate the TGC value of the ROI A3. When the user regulates the TGC regulating objects 702d', 702e', 702f', and 702g', the depth reference line R1 may be displayed or removed. That is, the user may view the entire ultrasound image through the display unit 160, view the ROI A3 of the ultrasound image through the sub display panel 161 at the same time, regulate the TGC regulating objects 702d', 702e', 702f', and 702g' corresponding thereto and regulate the TGC value of the ROI A3.

Also, it is needless to say that, unlike the above description, on the display unit 160, the enlarged ROI A3 of the ultrasound image and the TGC regulating objects 702d', 702e', 702f', and 702g' corresponding to the ROI may be displayed, and on the sub display panel 161, the entire ultrasound image of the subject, the TGC regulating object 700 and the TGC regulating line L1 may be displayed.

Figure 12:
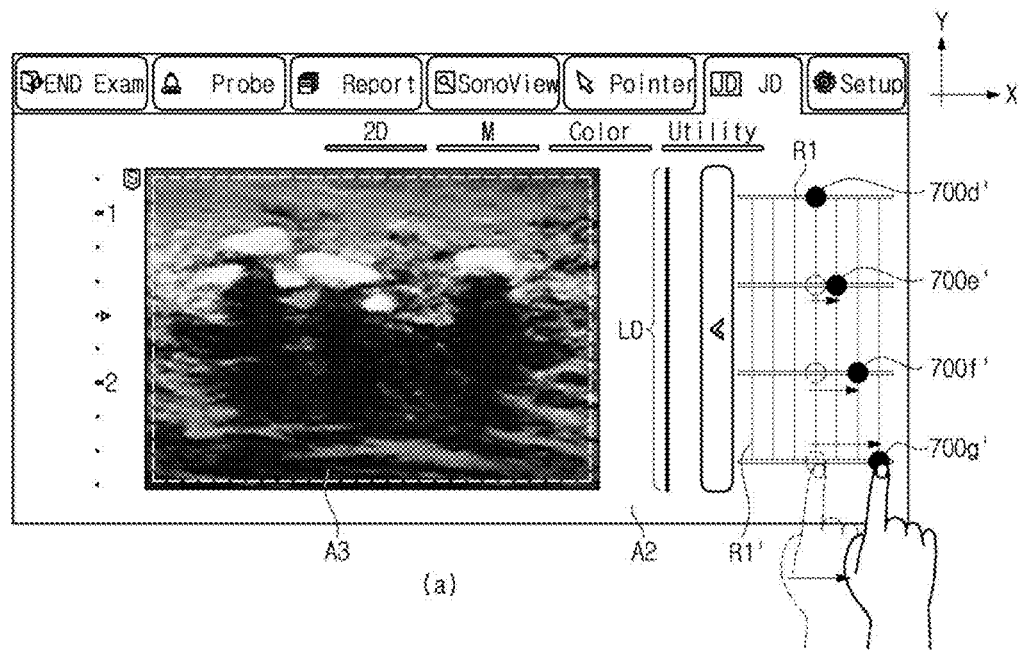
FIG. 12 is a diagram illustrating a case in which a TGC regulating unit corresponding to an ROI in an ultrasound image is touched and a TGC value is regulated according to an embodiment.
Figure 12:
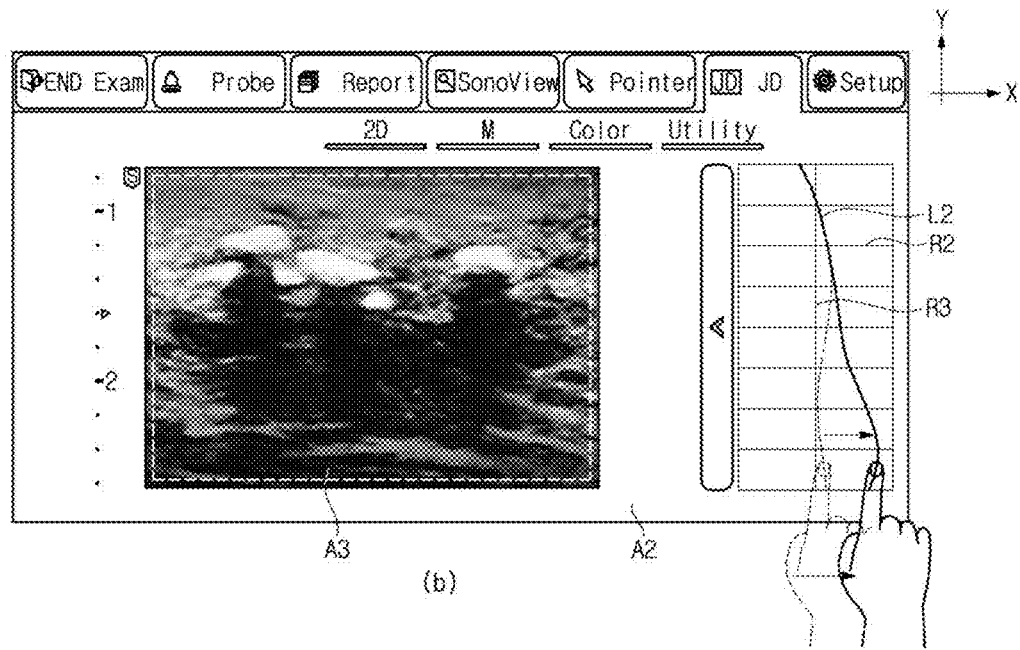

FIG. 12 is a diagram illustrating a case in which a TGC regulating unit corresponding to an ROI in an ultrasound image is touched and a TGC value is regulated according to an embodiment.

As illustrated in FIG. 12, an enlarged image of the ROI A3 of the ultrasound image and the TGC regulating unit corresponding thereto may be displayed on the display unit 160 or the sub display panel 161. The TGC regulating objects 700d', 700e', 700f', and 700g' corresponding to the ROI A3 are displayed in FIG. 12A. The TGC regulating line L2 corresponding to the ROI A3 is displayed in FIG. 12B. As illustrated in FIG. 12A, the user may regulate the TGC value of the ROI A3 by touching the TGC regulating objects 700d', 700e', 700f', and 700g'. Specifically, the user may drag the TGC regulating objects 700e', 700f', and 700g' of depths to be regulated of the ROI A3 among the TGC regulating objects 700d', 700e', 700f', and 700g' to levels to be regulated. Also, instead of dragging, by directly touching a position of a TGC level to be regulated, the TGC regulating object of a corresponding depth may be moved to the contacted position and thus the TGC value may be regulated. Also, when the TGC regulating objects 700d', 700e', 700f', and 700g' are regulated, the TGC regulating line LD corresponding to the ROI A3 of the ultrasound image may also be changed according to a depth of the image. FIG. 12A illustrates a case in which only the TGC regulating objects 700e', 700f', and 700g' of depths to be regulated among the TGC regulating objects 700d', 700e', 700f', and 700g' may be moved to the right, and the TGC value of the ROI A3 is regulated. That is, a part of the ROI A3 of depths corresponding to the regulated TGC regulating objects 700e', 700f', and 700g' may be displayed to be brighter.

As illustrated in FIG. 12B, the user may regulate the TGC value of the ROI A3 by touching the TGC regulating line L2. As described above in FIG. 9B, only the TGC regulating line L2 corresponding to the ROI A3 is displayed in FIG. 12B. The user may drag a part of the TGC regulating line of a depth to be regulated of the ROI A3 within the TGC regulating line L2 to a level to be regulated. Also, instead of dragging, by directly touching a position of a TGC level to be regulated, a curved line of the TGC regulating line of a corresponding depth is positioned to the contacted position, and the TGC value may be regulated.

Figure 13:
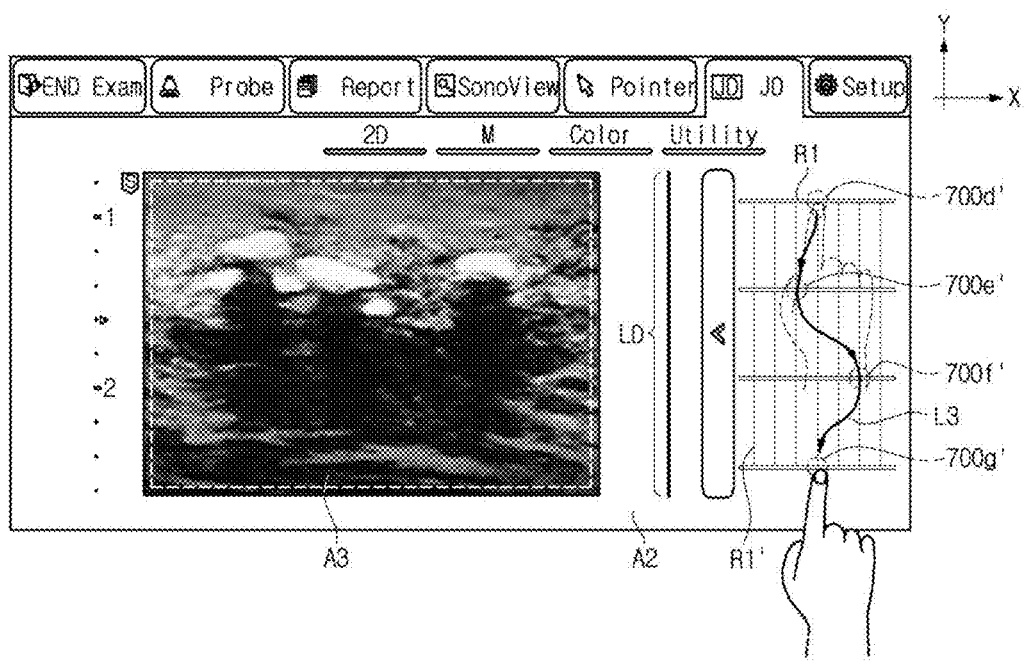
FIG. 13 is a diagram illustrating another embodiment in which a TGC regulating object corresponding to an ROI in an ultrasound image is manipulated and a TGC value is regulated.

FIG. 13 is a diagram illustrating another embodiment in which a TGC regulating object corresponding to an ROI in an ultrasound image is manipulated and a TGC value is regulated.

Unlike description in FIG. 12A, the user may regulate the TGC value by drawing a line on a screen in which the TGC regulating objects 700d', 700e', 700f', and 700g' are positioned as illustrated in FIG. 13. That is, when the user designates start points and end points of the TGC regulating objects 700d', 700e', 700f', and 700g' and draws a line L3 connecting the points, a finger is positioned along the line L3 along which the TGC regulating objects 700d', 700e', 700f', and 700g' are drawn and the TGC value may be regulated. In this case, the line may include a curved line and a straight line.

Figure 14A:
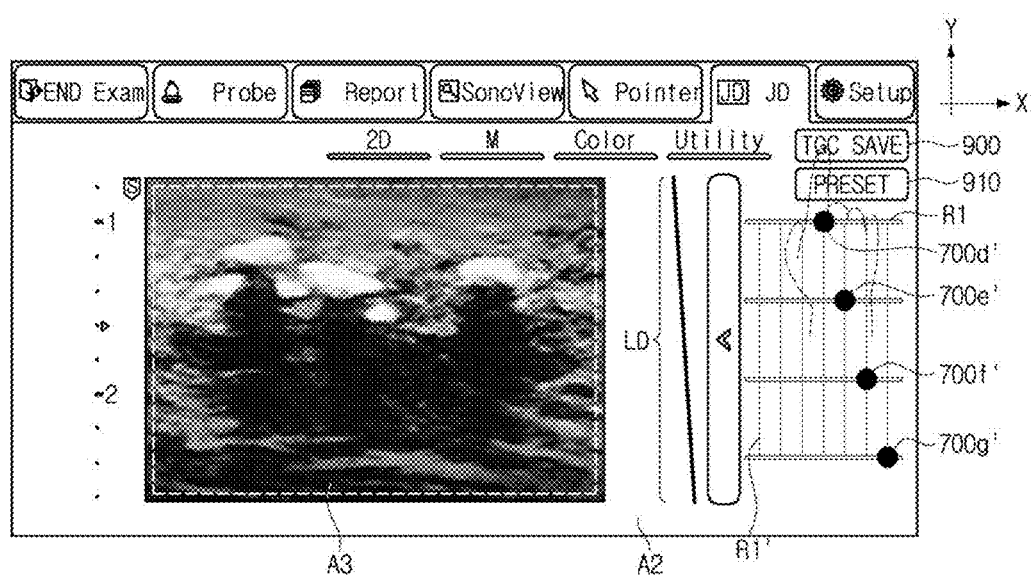
FIG. 14A is a diagram illustrating a case in which a TGC value regulated with respect to an ROI is stored in a memory according to an embodiment.
Figure 14B:
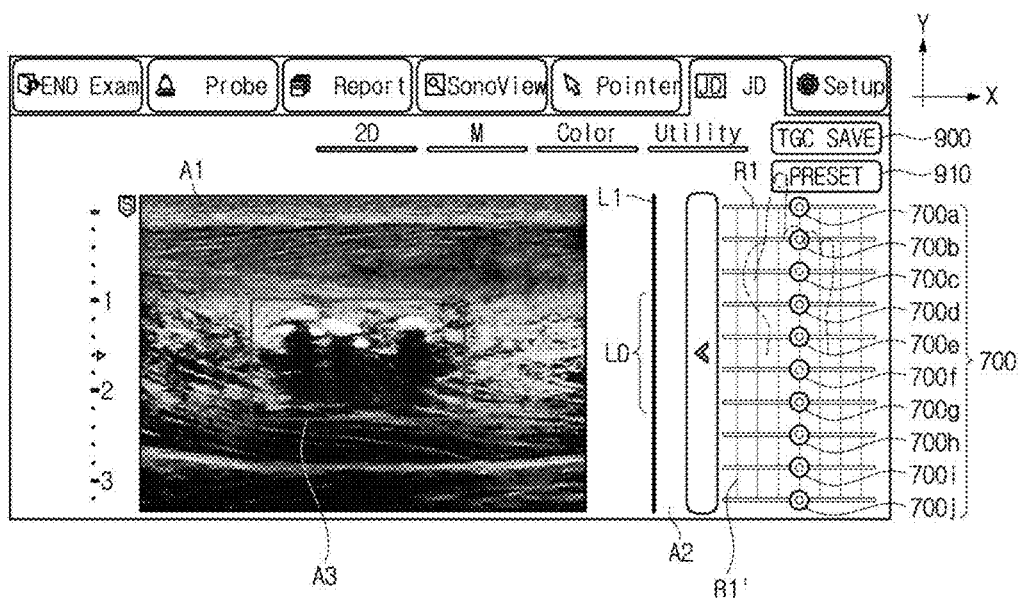
FIG. 14B is a diagram illustrating a case in which a TGC value that is regulated with respect to an ROI and stored is loaded from a memory according to an embodiment.

FIG. 14A is a diagram illustrating a case in which a TGC value regulated with respect to an ROI is stored in a memory according to an embodiment. FIG. 14B is a diagram illustrating a case in which a TGC value that is regulated with respect to an ROI and stored is loaded from a memory according to an embodiment.

Similar to FIG. 12A, FIG. 14A shows a screen in which the ROI A3 and the TGC regulating objects 700d', 700e', 700f', and 700g' corresponding thereto are manipulated and the TGC value is regulated.

The user may touch a TGC save button 900 displayed on the second region A2 and store the TGC value regulated with respect to the ROI A3. That is, the TGC value, set by the user, with respect to the ROI A3 is stored in the memory 600, and when observation of the same ROI A3 is desired again later, the value may be loaded and used.

FIG. 14B shows a screen when a preset button 910 is touched in order to load the TGC value stored in FIG. 14A while an entire screen of the ultrasound image is displayed. As described above, a region that can be set as the ROI by the user in the entire screen of the ultrasound image is not limited. When the preset button 910 is touched in order to enlarge again and view the screen of the ROI A3 set in FIG. 14A, a screen to which the TGC value regulated with respect to the ROI A3 is applied may be displayed. This TGC value may be stored in the memory 600. The user may initialize the stored TGC value through the input unit 150, the display unit 160 or the sub display panel 161 or may store a TGC value for another ROI.

Figure 15:
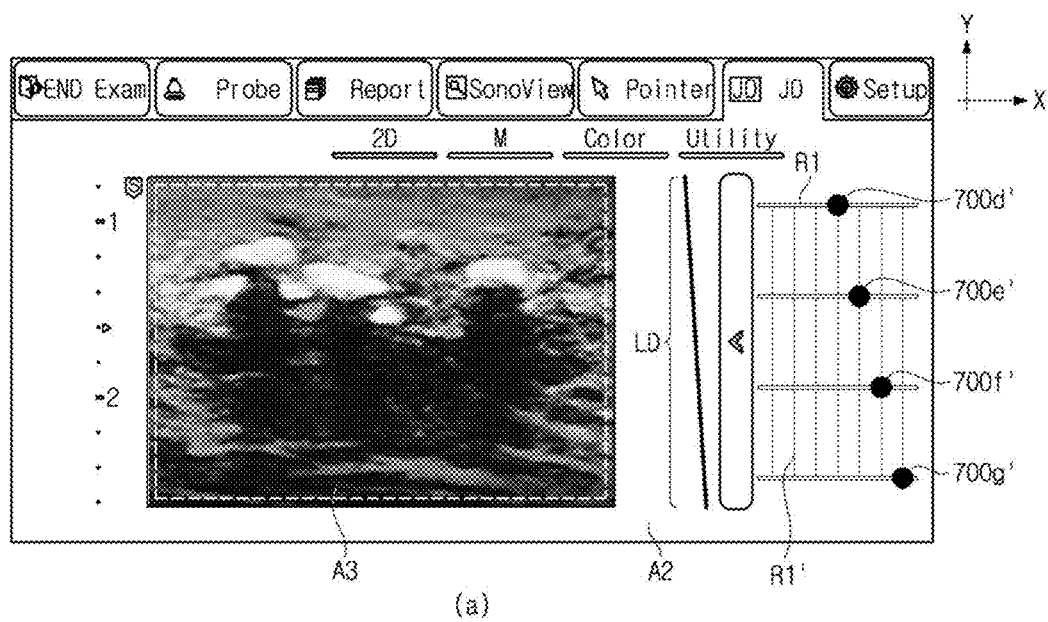
FIG. 15 is a diagram illustrating an ROI when a TGC value of an ROI in an ultrasound image is regulated and then restoring to an entire region is performed according to an embodiment.
Figure 15:
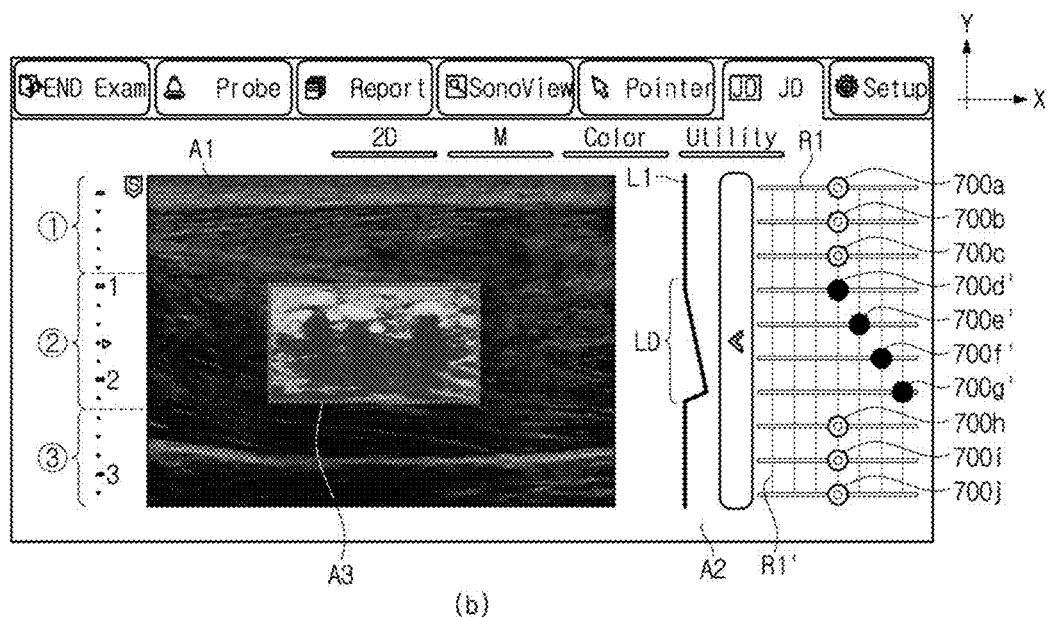

FIG. 15 is a diagram illustrating an ROI when a TGC value of an ROI in an ultrasound image is regulated and then restoring to an entire region is performed according to an embodiment.

FIG. 15A shows a screen when the TGC value with respect to the ROI A3 is regulated as described in FIG. 12A. FIG. 15B shows a screen when the TGC regulated with respect to the ROI A3 is applied to an entire screen as described in FIG. 2A.

That is, as in FIG. 2A, when a part including the ROI A3 is dark and slightly invisible in the entire ultrasound image of the subject, the user may regulate the TGC regulating objects 700d', 700e', 700f', and 700g' and increase a definition of the ROI A3. After regulation of the TGC with respect to the ROI A3 is completed, the regulated TGC value may be stored in the memory 600. When the user wants to view the entire ultrasound image including the ROI A3, the image may be restored to an entire image before the ROI A3 is enlarged as in FIG. 15B. Also, in the displayed TGC regulating objects, the TGC regulating objects 700d', 700e', 700f', and 700g' in which the TGC value with respect to the ROI A3 is regulated may be displayed, and the TGC regulating objects 700a, 700b, 700c, 700h, 700i, and 700j in which a TGC value is not regulated with respect to a region other than the ROI A3 may be displayed.

In this case, since the TGC value of the ROI A3 is regulated, the ROI A3 part may be brightly displayed, and a part other than the ROI A3 may be darkly displayed as illustrated in FIG. 15B. When the ROI A3 part in which the TGC value is regulated is restored to the entire screen, since a connection with the part other than the ROI A3 may be unsuccessful, the ROI A3 may be restored while the regulated TGC value is or is not applied.

As another embodiment unlike FIG. 15, when the ultrasound image in which the TGC value with respect to the ROI A3 is regulated is restored to an entire screen before enlargement, restoration may be performed while a TGC value of an entire region in an X axis direction including the ROI A3 is regulated. That is, when FIG. 15A is restored to the entire ultrasound image in FIG. 15B, the TGC regulating value may also be applied to an entire region ② in the X axis direction including the ROI A3 and then displayed. In this case, the screen may be displayed as the screen shown in FIG. 2B.

As still another embodiment, there may be another ROI (not illustrated) set by the user. When the TGC value with respect to another ROI (not illustrated) is regulated and then restoring to the entire screen is performed, the TGC regulating object may be changed to correspond to a corresponding region and then displayed.

The user may move or reduce the set ROI A3, or reset by further enlarging, expanding, or rotating. When the reset or changed ROI A3 is restored to the entire screen, the TGC regulating unit may be changed to correspond to the reset or changed ROI A3 and then displayed. Also, the TGC regulating unit to be applied may be differently set for the same ROI A3. In this case, when restoring to the entire screen is performed, the set TGC regulating unit may be changed and then displayed.

Figure 16:
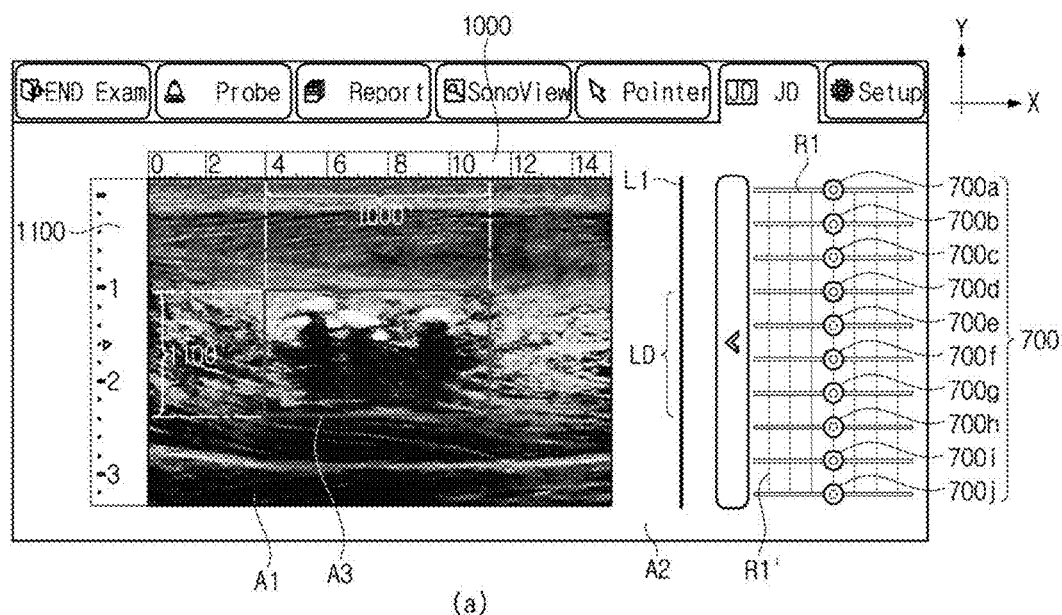
FIG. 16 is a diagram illustrating a case in which gradations in X and Y directions of an ROI are enlarged and displayed when the ROI in an ultrasound image is set and enlarged according to an embodiment.
Figure 16:
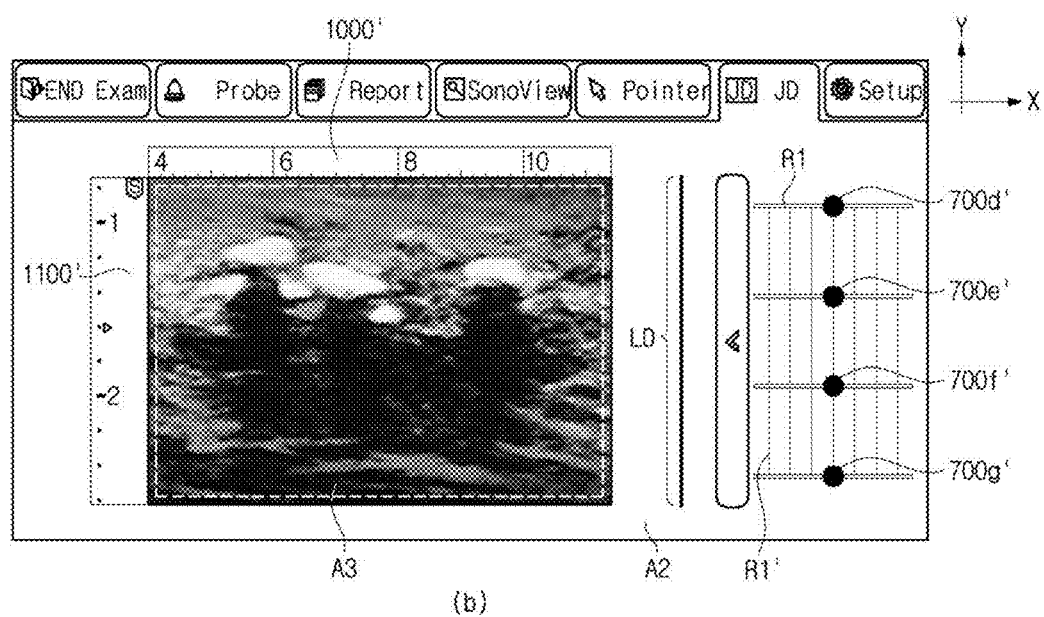

FIG. 16 is a diagram illustrating a case in which gradations in X and Y directions of an ROI are enlarged and displayed when the ROI in an ultrasound image is set and enlarged according to an embodiment.

As illustrated in FIG. 16A, before the ROI A3 of the ultrasound image is set, a gradation 1000 in an X axis direction is graded from 0 to 15.2, and a gradation 1100 in a Y axis direction is graded from 0 to 3.4. A shape of the gradation displayed on the ultrasound image and a scale value thereof are not limited to those in FIG. 16, but various embodiments are available. When the user set and enlarges the ROI A3, it can be displayed as in FIG. 16B. In this case, the gradations in the X axis and Y axis directions may be changed to correspond to the enlarged ROI A3. That is, a gradation 1000' in an X axis direction of the enlarged ROI A3 may be graded from 4 to 11.4 corresponding to the ROI A3, and a gradation 1100' in a Y axis direction may be graded from 1 to 2.4. That is, there is an effect in which a size and a region of the ROI A3 set by the user may be more intuitively identified.

While the embodiments of the disclosed invention have been described based on an application of a 2D ultrasound image, although not illustrated, display of the TGC regulating object of the disclosed invention may be applied to a 3D ultrasound image. In the embodiments of the ultrasound imaging apparatus described above, gain compensation in a depth direction (Y axis direction) of the ultrasound image is defined as time gain compensation, and gain compensation in a lateral (horizontal) direction (X axis direction) is defined as lateral gain compensation. When gain compensation in a Z axis direction is defined as elevation gain compensation (EGC), gain compensation regulation of the 3D ultrasound image may be regulated as TGC, LGC or EGC values. Therefore, when the embodiment of the disclosed invention is applied to the 3D ultrasound image, the gain compensation regulating unit may be displayed with respect to X, Y and Z axes of the region set as the ROI.

Figure 17:
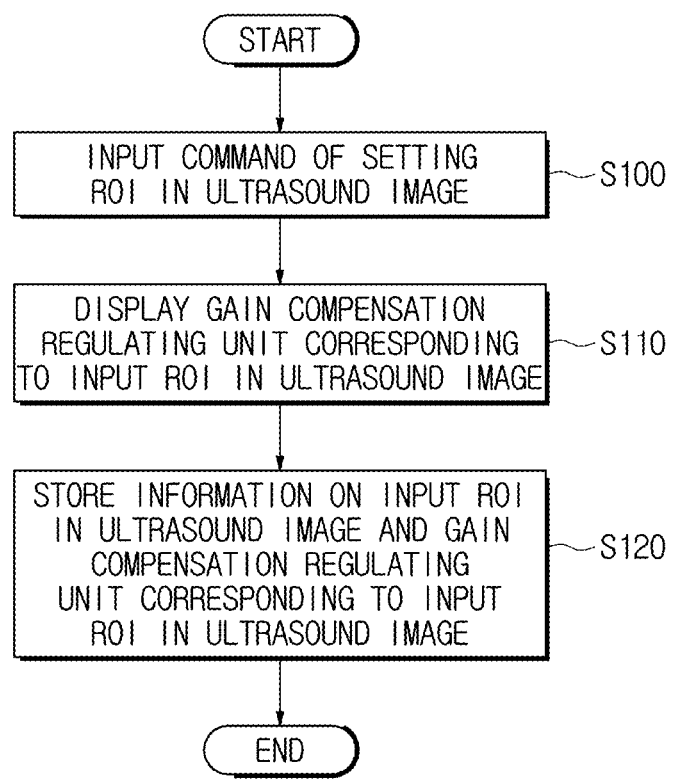
FIG. 17 is a flowchart illustrating a method of controlling an ultrasound imaging apparatus according to an embodiment.

FIG. 17 is a flowchart illustrating a method of controlling an ultrasound imaging apparatus according to an embodiment.

As illustrated in FIG. 17, the user may input a command of setting the ROI A3 of the ultrasound image (S100). That is, the user may set the ROI A3 through the input unit 150 or input a command of setting the ROI A3 by touching the display unit 160 or the sub display panel 161. The input command of setting the ROI A3 may be stored in the memory 600. The processor 400 may perform control such that the gain compensation regulating unit corresponding thereto may be displayed on the display unit 160 or the sub display panel based on the input ROI A3 setting.

The display unit 160 or the sub display panel 161 may display the gain compensation regulating unit corresponding to the input ROI A3 of the ultrasound image (S110). As described above, the gain compensation regulating unit may include at least one of the TGC regulating unit and the LGC regulating unit, and a display mode may include various embodiments.

The memory 600 may store information on the input ROI A3 of the ultrasound image and the gain compensation regulating unit corresponding to the input ROI A3 of the ultrasound image (S120). The information on the ROI A3 and the gain compensation regulating unit stored in the memory 600 may be used when the set ROI A3 is loaded or a gain compensation regulating value corresponding thereto is applied.

The above-described embodiments in which the ROI A3 of the ultrasound image is set and the gain compensation regulating unit corresponding thereto is displayed may be similarly applied when the ROI A3 is enlarged or reduced. Various embodiments in which the ROI in the ultrasound image has a different size and shape are available in addition to the above-described embodiments.

When a TGC or LGC regulating unit of the ROI to be observed by the user in the ultrasound image of the subject is displayed, there are effects in which unnecessary display of the TGC or LGC regulating unit of a part that is not set as the ROI is prevented, and the TGC or LGC value of the ROI can be regulated accurately and precisely.

Exemplary embodiments of the ultrasound imaging apparatus and the method of controlling the same have been described above with reference to the exemplary drawings. Examples of the ultrasound imaging apparatus and the method of controlling the same are not limited thereto. The above-described embodiments are only examples in all aspects. Therefore, it will be understood by those skilled in the art that the invention may be performed in other concrete forms without changing the technological scope and essential features. Therefore, the scope of the present invention is defined not by the detailed description but by the appended claims. All modifications and equivalents that fall within the scope of the appended claims will be construed as being included in the present invention.

What is claimed is:

1. An ultrasound imaging apparatus, comprising:
an input unit configured to receive a command of setting a region of interest (ROI) in an ultrasound image;
a display unit including a first region on which the ultrasound image is displayed and a second region on which a gain compensation regulating unit configured to change a gain compensation value of the ultrasound image is displayed; and
a processor configured to display an enlarged ROI in the ultrasound image on the first region and display only the gain compensation regulating unit corresponding to the enlarged ROI in the ultrasound image on the second region, when the command of setting the ROI in the ultrasound image displayed on the first region of the display unit is input,
wherein the processor is configured to determine a number of the gain compensation regulating unit displayed on the second region and a range thereof based on the enlarged ROI.

2. The ultrasound imaging apparatus according to claim 1,
wherein the ROI in the ultrasound image is a region set by enlarging, reducing, expanding or rotating the ultrasound image, and
when the ROI is set, a screen displayed on the display unit is changed.

3. The ultrasound imaging apparatus according to claim 1,
wherein the gain compensation regulating unit includes at least one of a time gain compensation (TGC) regulating unit and a lateral gain compensation (LGC) regulating unit.

4. The ultrasound imaging apparatus according to claim 1,
wherein the display unit displays an increased or decreased level of the gain compensation regulating unit corresponding to the ROI in the ultrasound image such that gain compensation of the ROI in the ultrasound image is finely regulated.

5. The ultrasound imaging apparatus according to claim 1,
wherein the display unit emphasizes and displays a display mode of the gain compensation regulating unit corresponding to the ROI in the ultrasound image, and emphasizing and displaying the gain compensation regulating unit includes displaying the gain compensation regulating unit corresponding to the ROI in the ultrasound image by changing a color thereof.

6. The ultrasound imaging apparatus according to claim 1,
wherein the display unit displays the ROI in the ultrasound image on the first region and displays the ROI in the ultrasound image and the gain compensation regulating unit corresponding to the ROI in the ultrasound image in an overlapping manner.

7. The ultrasound imaging apparatus according to claim 1,
wherein the command of setting the ROI in the ultrasound image includes a command of enlarging or reducing a specific area in the ultrasound image.

8. The ultrasound imaging apparatus according to claim 1, further comprising a sub display panel configured to display an ultrasound image set as the ROI and the gain compensation regulating unit corresponding to the ROI in the ultrasound image,
wherein the display unit displays an entire ultrasound image before the ROI in the ultrasound image is set and a gain compensation regulating unit corresponding thereto, and
wherein the sub display panel displays the ROI in the ultrasound image and the gain compensation regulating unit corresponding to the ROI in the ultrasound image.

9. The ultrasound imaging apparatus according to claim 8,
wherein the sub display panel displays the ROI in the ultrasound image and the gain compensation regulating unit corresponding to the ROI in the ultrasound image in an overlapping manner.

10. The ultrasound imaging apparatus according to claim 8,
wherein the display unit and the sub display panel include a touch panel in which a user inputs a touch command of setting the ROI in the ultrasound image and touches the gain compensation regulating unit corresponding to the ROI in the displayed ultrasound image and thus the gain compensation value corresponding to the ultrasound image set as the ROI is regulated.

11. The ultrasound imaging apparatus according to claim 3,
wherein the display unit displays at least one of a TGC regulating unit configured to regulate a TGC value corresponding to a depth direction of the ultrasound image set as the ROI and an LGC regulating unit configured to regulate an LGC value corresponding to a lateral direction.

12. The ultrasound imaging apparatus according to claim 11,
wherein the display unit displays at least one of a TGC regulating object and a TGC regulating line configured to regulate a TGC value corresponding to a depth direction of the ultrasound image set as the ROI.

13. The ultrasound imaging apparatus according to claim 11,
wherein the display unit displays at least one of an LGC regulating object and an LGC regulating line configured to regulate an LGC value corresponding to a lateral direction of the ultrasound image set as the ROI.

14. The ultrasound imaging apparatus according to claim 1, further comprising
a memory configured to store information on the input ROI in the ultrasound image and the gain compensation regulating unit corresponding to the input ROI in the ultrasound image.

15. A method of controlling an ultrasound imaging apparatus including a display unit having a first region on which an ultrasound image is displayed and a second region on which a gain compensation regulating unit configured to change a gain compensation value of the ultrasound image is displayed, the method comprising:
receiving a command of setting a region of interest (ROI) in the ultrasound image displayed on the first region;
displaying an enlarged ROI on the first region; and
displaying only a gain compensation regulating unit corresponding to the enlarged ROI in the ultrasound image on the second region,
wherein the displaying of only the gain compensation regulating unit corresponding to the enlarged ROI comprises determining a number of the gain compensation regulating unit displayed on the second region and a range thereof based on the enlarged ROI.

16. The method according to claim 15,
wherein the displaying of the gain compensation regulating unit corresponding to the input ROI in the ultrasound image includes
displaying an increased or decreased level of the gain compensation regulating unit corresponding to the ROI in the ultrasound image such that gain compensation of the ROI in the ultrasound image is finely regulated.

17. The method according to claim 15,
wherein the displaying of the gain compensation regulating unit corresponding to the input ROI in the ultrasound image includes emphasizing and displaying a display mode of the gain compensation regulating unit corresponding to the ROI in the ultrasound image, and
the emphasizing and displaying of the gain compensation regulating unit includes displaying the gain compensation regulating unit corresponding to the ROI in the ultrasound image by changing a color thereof.

18. The method according to claim 15,
wherein the displaying of the gain compensation regulating unit corresponding to the input ROI in the ultrasound image includes
displaying the ROI in the ultrasound image displayed on the first region and the gain compensation regulating unit corresponding to the ROI in the ultrasound image in an overlapping manner.

19. The method according to claim 15,
wherein the receiving of the command of setting the ROI in the ultrasound image includes a command of enlarging or reducing a specific area in the ultrasound image.

20. The method according to claim 15,
wherein the gain compensation regulating unit includes at least one of a time gain compensation (TGC) regulating unit and a lateral gain compensation (LGC) regulating unit, and
wherein the displaying of the gain compensation regulating unit corresponding to the input ROI in the ultrasound image includes displaying at least one of a TGC regulating unit configured to regulate a TGC value corresponding to a depth direction of the ultrasound image set as the ROI and an LGC regulating unit configured to regulate an LGC value corresponding a lateral direction.

21. The method according to claim 20,
wherein the displaying of the TGC regulating unit corresponding to the input ROI in the ultrasound image includes displaying at least one of a TGC regulating object and a TGC regulating line configured to regulate a TGC value corresponding to a depth direction of the ultrasound image set as the ROI.

22. The method according to claim 20,
wherein the displaying of the LGC regulating unit corresponding to the input ROI in the ultrasound image includes displaying at least one of an LGC regulating object and an LGC regulating line configured to regulate an LGC value corresponding to a lateral direction in the ultrasound image set as the ROI.

23. The method according to claim 15, further comprising
storing information on the input ROI in the ultrasound image and the gain compensation regulating unit corresponding to the input ROI in the ultrasound image.

24. The ultrasound imaging apparatus according to claim 1,
wherein the processor is further configured to determine a depth of the gain compensation regulating unit displayed on the second region based on a depth of the input ROI in the ultrasound image.

25. The ultrasound imaging apparatus according to claim 1,
wherein the processor is further configured to determine a density of the gain compensation regulating unit displayed on the second region based on an enlargement ration of the enlarged ROI in the ultrasound image.

* * * * *